United States Patent
McCrea et al.

(10) Patent No.: US 9,241,708 B2
(45) Date of Patent: Jan. 26, 2016

(54) LARGE BORE CLOSURE DEVICE AND METHODS

(75) Inventors: James A. McCrea, Burlingame, CA (US); Troy T. White, Maple Grove, MN (US); Bernhard Kaeferlein, Champlin, MN (US); Ali Hassan, Palo Alto, CA (US); Jason M. Halac, Solana Beach, CA (US); Zihan Lin, Irvine, CA (US); Zachary J. Tegels, Minneapolis, MN (US); Martha Escobar, Jordan, MN (US); Catherine A. Pipenhagen, Chanhassen, MN (US)

(73) Assignee: ST. JUDE MEDICAL PUERTO RICO, LLC, Caguas, PR (US)

( * ) Notice: Subject to any disclaimer, the term of this patent is extended or adjusted under 35 U.S.C. 154(b) by 143 days.

(21) Appl. No.: 13/490,816

(22) Filed: Jun. 7, 2012
(Under 37 CFR 1.47)

(65) Prior Publication Data

US 2013/0144316 A1    Jun. 6, 2013

Related U.S. Application Data

(60) Provisional application No. 61/494,345, filed on Jun. 7, 2011.

(51) Int. Cl.
  *A61B 17/04* (2006.01)
  *A61B 17/00* (2006.01)
  *A61B 17/06* (2006.01)

(52) U.S. Cl.
  CPC ......... *A61B 17/0469* (2013.01); *A61B 17/0057* (2013.01); *A61B 17/0482* (2013.01);
  (Continued)

(58) Field of Classification Search
  CPC .. A61B 17/04; A61B 17/0483; A61B 17/062; A61B 17/0057; A61B 2017/0472; A61B 2017/00637; A61B 17/0482; A61B 17/3403; A61B 2017/06057; A61B 2017/06052
  USPC .......................................... 606/144–150, 139
  See application file for complete search history.

(56) References Cited

U.S. PATENT DOCUMENTS 3,470,875 A    10/1969 Johnson
5,431,666 A    7/1995 Sauer et al.
(Continued)

FOREIGN PATENT DOCUMENTS

EP    0818178 A2    1/1998
EP    1158907 A1    12/2001
(Continued)

OTHER PUBLICATIONS

Notification of Transmittal of the International Search Report and the Written Opinion of the International Searching Authority, or the Declaration for International Application No. PCT/US2012/064768, mailed Feb. 19, 2013, (18 pp.).
(Continued)

*Primary Examiner* — Katherine Rodjom
(74) *Attorney, Agent, or Firm* — Holland & Hart

(57) ABSTRACT

A vascular closure system includes a body portion, an anchor, a suture carrying portion, and a plurality of needles. The body portion has a distal end surface. The anchor is positionable through a vessel puncture in a vessel wall of a vessel. The anchor defines a vessel contact surface, wherein withdrawal of the anchor captures a portion of the vessel wall between the vessel contact surface and the distal end surface. The suture carrying portion is positionable through the vessel puncture and carries at least one suture member. The plurality of needles extend through the portion of the vessel wall adjacent to the vessel puncture and are configured to connect to the at least one suture member. Withdrawal of the plurality of needles through the portion of the vessel wall positions the at least one suture member through the portion of the vessel wall.

33 Claims, 18 Drawing Sheets

(52) U.S. Cl.
CPC .......... *A61B2017/00663* (2013.01); *A61B 2017/0472* (2013.01); *A61B 2017/0496* (2013.01); *A61B 2017/06042* (2013.01)

(56) References Cited

U.S. PATENT DOCUMENTS

| | | | |
|---|---|---|---|
| 5,520,702 A | 5/1996 | Sauer et al. | |
| 5,562,686 A | 10/1996 | Sauer et al. | |
| 5,613,974 A | 3/1997 | Andreas et al. | |
| 5,643,292 A * | 7/1997 | Hart | 606/144 |
| 5,674,231 A | 10/1997 | Green et al. | |
| 5,700,273 A * | 12/1997 | Buelna et al. | 606/148 |
| 5,709,692 A | 1/1998 | Mollenauer et al. | |
| 5,728,114 A | 3/1998 | Evans et al. | |
| 5,766,183 A | 6/1998 | Sauer | |
| 5,860,990 A | 1/1999 | Nobles et al. | |
| 5,972,005 A | 10/1999 | Stalker et al. | |
| 6,036,699 A | 3/2000 | Andreas et al. | |
| 6,048,357 A | 4/2000 | Kontos | |
| 6,059,800 A | 5/2000 | Hart et al. | |
| 6,136,010 A | 10/2000 | Modesitt et al. | |
| 6,355,050 B1 | 3/2002 | Andreas et al. | |
| 6,562,052 B2 | 5/2003 | Nobles et al. | |
| 6,641,592 B1 | 11/2003 | Sauer et al. | |
| 6,896,692 B2 | 5/2005 | Ginn et al. | |
| 6,911,034 B2 | 6/2005 | Nobles et al. | |
| 6,932,824 B1 | 8/2005 | Roop et al. | |
| 6,964,668 B2 | 11/2005 | Modesitt et al. | |
| 6,969,397 B2 | 11/2005 | Ginn | |
| 7,001,400 B1 | 2/2006 | Modesitt et al. | |
| 7,083,635 B2 | 8/2006 | Ginn | |
| 7,235,087 B2 | 6/2007 | Modesitt et al. | |
| 7,361,183 B2 | 4/2008 | Ginn | |
| 7,390,328 B2 | 6/2008 | Modesitt | |
| 7,553,319 B2 | 6/2009 | Bagaoisan et al. | |
| 7,601,161 B1 | 10/2009 | Nobles et al. | |
| 7,621,937 B2 | 11/2009 | Pipenhagen et al. | |
| 7,686,821 B2 | 3/2010 | Hathaway et al. | |
| 7,731,726 B2 | 6/2010 | Belhe et al. | |
| 7,744,610 B2 | 6/2010 | Hausen | |
| 7,752,853 B2 | 7/2010 | Singh et al. | |
| 7,753,933 B2 | 7/2010 | Ginn et al. | |
| 7,837,696 B2 | 11/2010 | Modesitt et al. | |
| 7,842,047 B2 | 11/2010 | Modesitt et al. | |
| 7,842,048 B2 | 11/2010 | Ma | |
| 7,846,170 B2 | 12/2010 | Modesitt et al. | |
| 7,850,701 B2 | 12/2010 | Modesitt et al. | |
| 7,883,517 B2 | 2/2011 | Pantages et al. | |
| 7,985,240 B2 | 7/2011 | Bagaoisan et al. | |
| 8,029,476 B2 | 10/2011 | Rosenberg et al. | |
| 8,083,768 B2 | 12/2011 | Ginn et al. | |
| 8,192,456 B2 | 6/2012 | Holman et al. | |
| 2002/0077658 A1 | 6/2002 | Ginn | |
| 2005/0085854 A1 | 4/2005 | Ginn | |
| 2006/0212071 A1 | 9/2006 | Ginn et al. | |
| 2008/0065151 A1 | 3/2008 | Ginn | |
| 2009/0099578 A1 | 4/2009 | Heneveld et al. | |
| 2009/0306685 A1 | 12/2009 | Fill | |
| 2010/0042118 A1 | 2/2010 | Garrison et al. | |
| 2011/0071567 A1 | 3/2011 | Modesitt et al. | |
| 2011/0077670 A1 | 3/2011 | Modesitt et al. | |

FOREIGN PATENT DOCUMENTS

| | | |
|---|---|---|
| EP | 1327419 A2 | 7/2003 |
| EP | 1349501 A2 | 10/2003 |
| EP | 1677682 A2 | 7/2006 |
| EP | 1972282 A2 | 9/2008 |
| EP | 2147640 A2 | 1/2010 |
| EP | 2298180 A1 | 3/2011 |
| WO | 9703613 | 2/1997 |
| WO | 0051498 | 9/2000 |
| WO | 0078226 A1 | 12/2000 |
| WO | 2010081106 A1 | 7/2010 |

OTHER PUBLICATIONS

Notification of Transmittal of the International Search Report and the Written Opinion of the International Searching Authority, or the Declaration for International Application No. PCT/US2012/066012, mailed Feb. 19, 2013, (17 pp.).

Notification of Transmittal of the International Search Report and the Written Opinion of the International Searching Authority, or the Declaration for International Application No. PCT/US2012/064770, mailed Feb. 19, 2013, (16 pp.).

PCT Communication Relating to the Results of the Partial International Search for International Application No. PCT/US2012/041196, mailed Sep. 11, 2012.

* cited by examiner

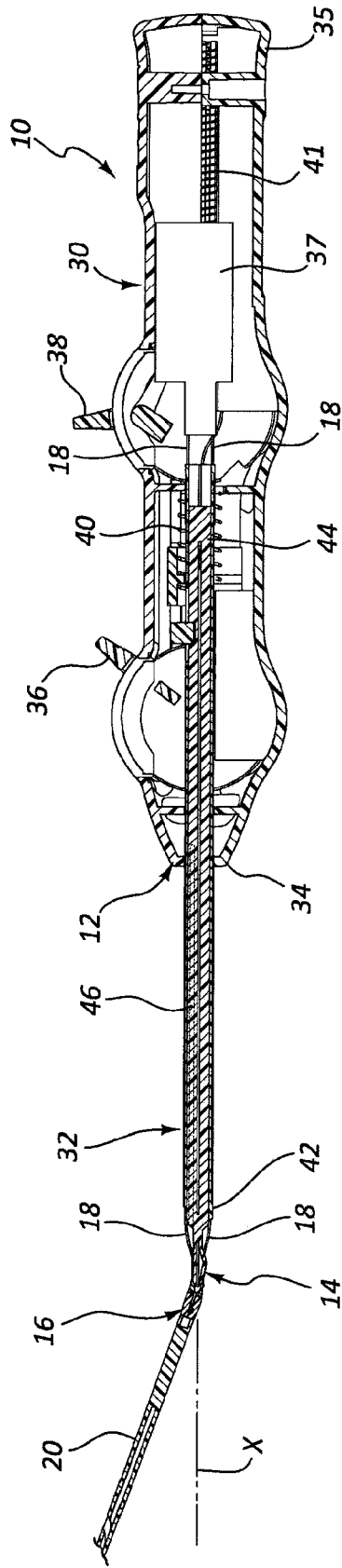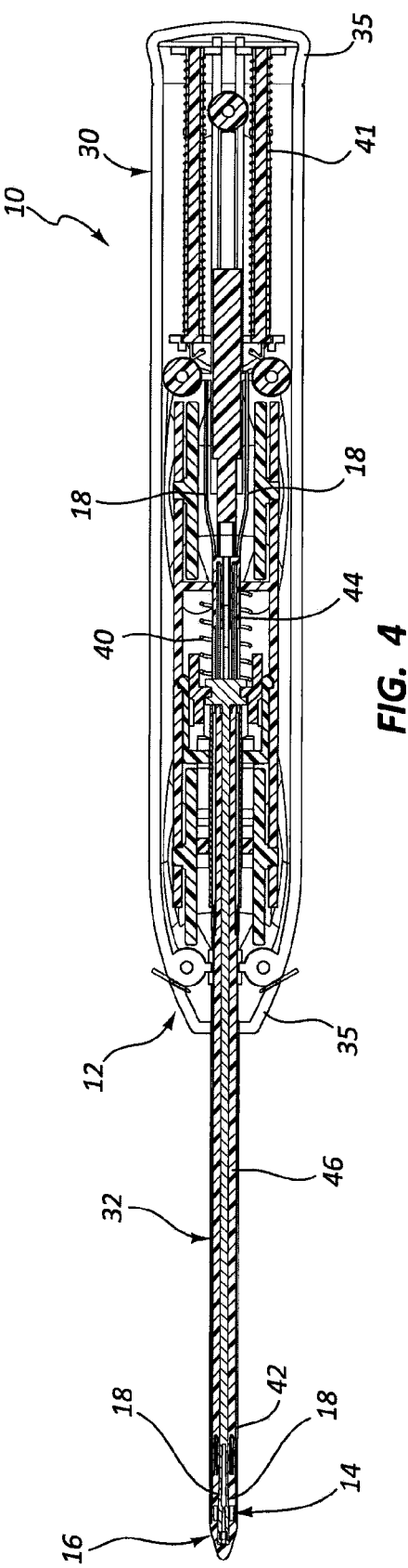
FIG. 3
FIG. 4

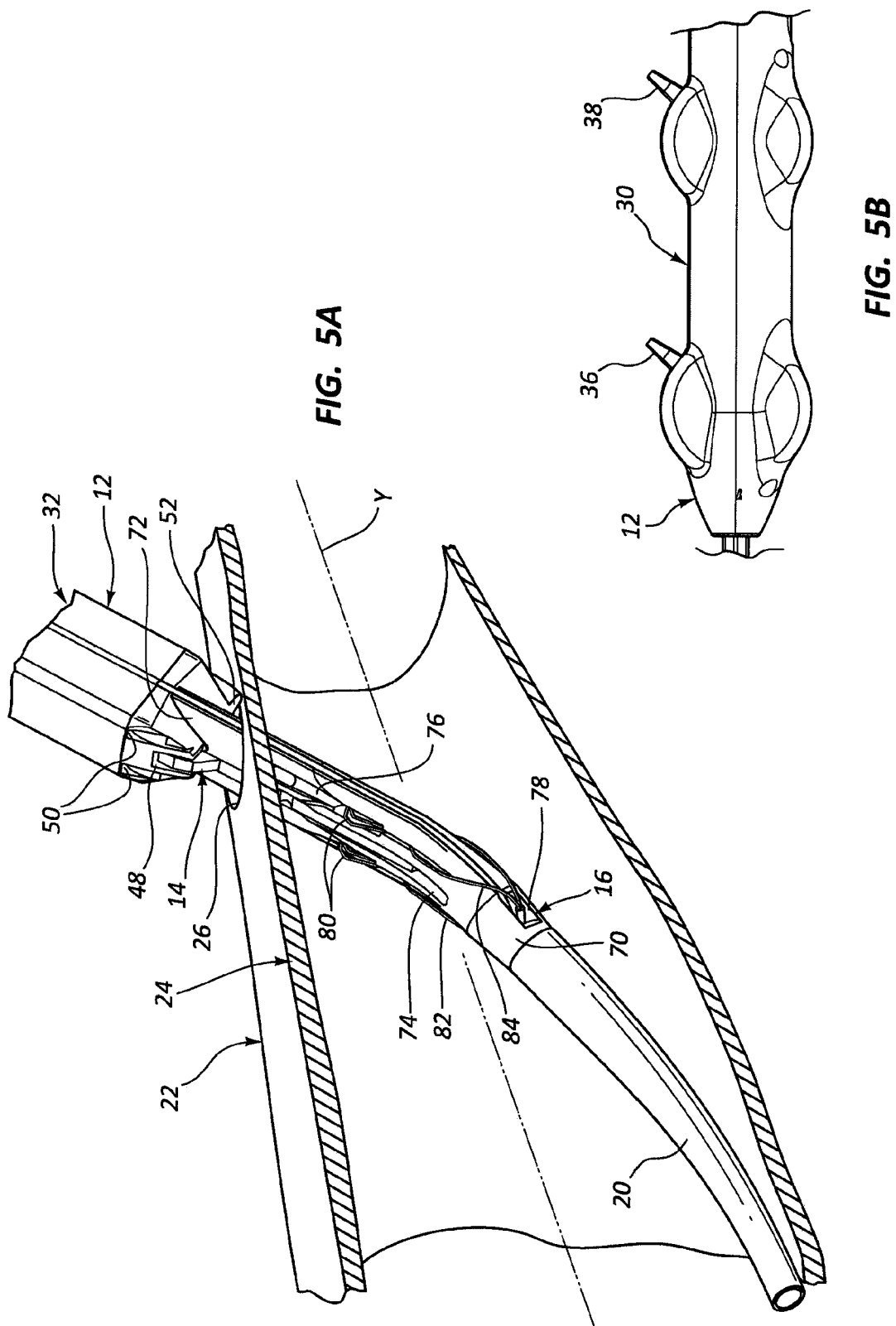

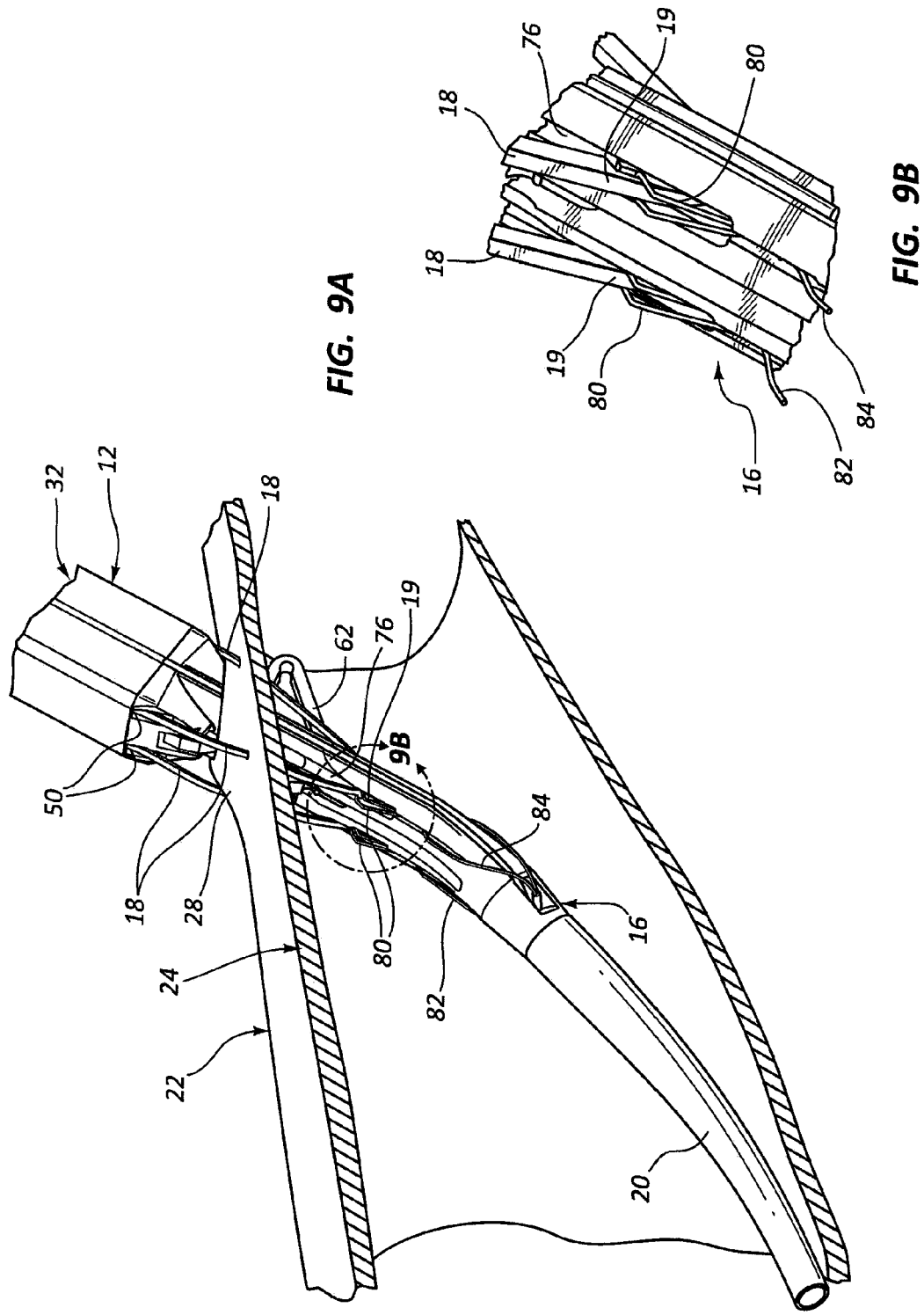

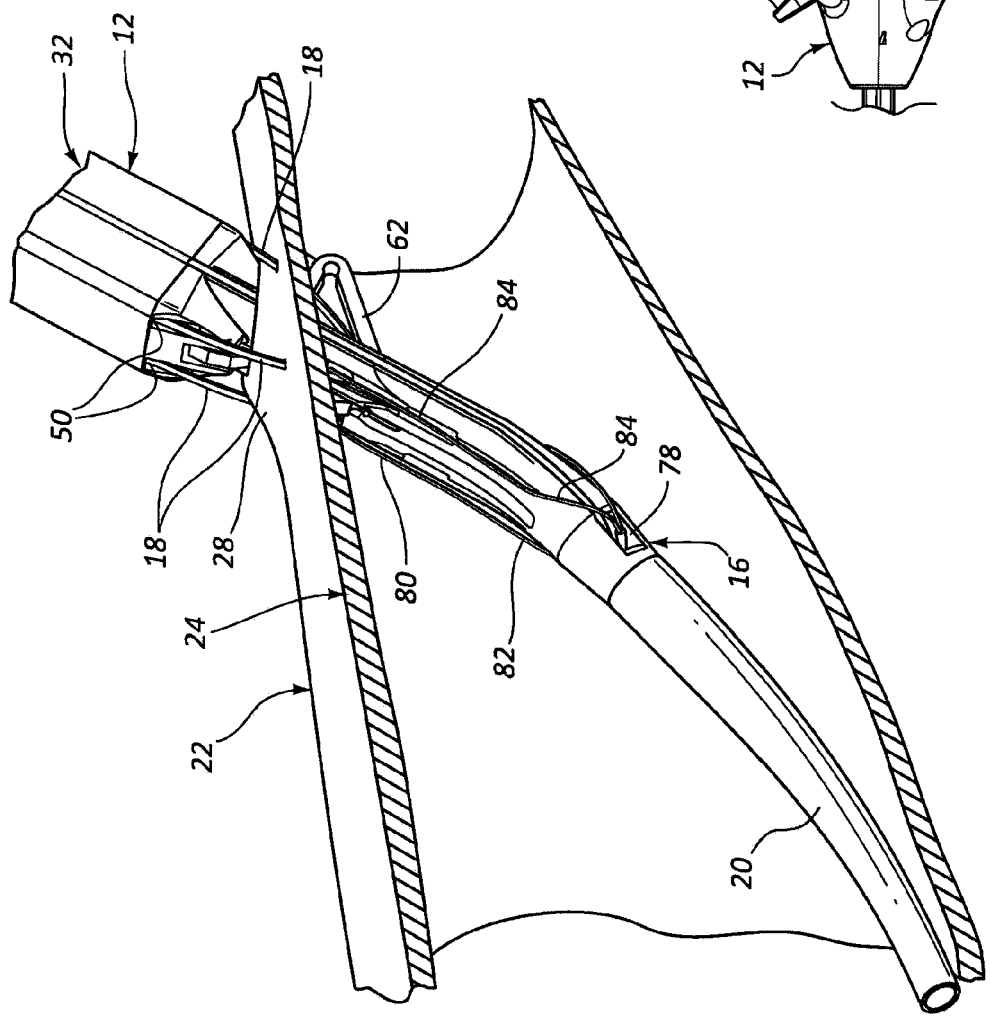
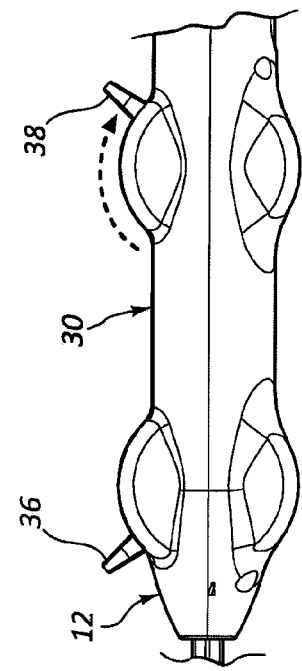
FIG. 10A
FIG. 10B

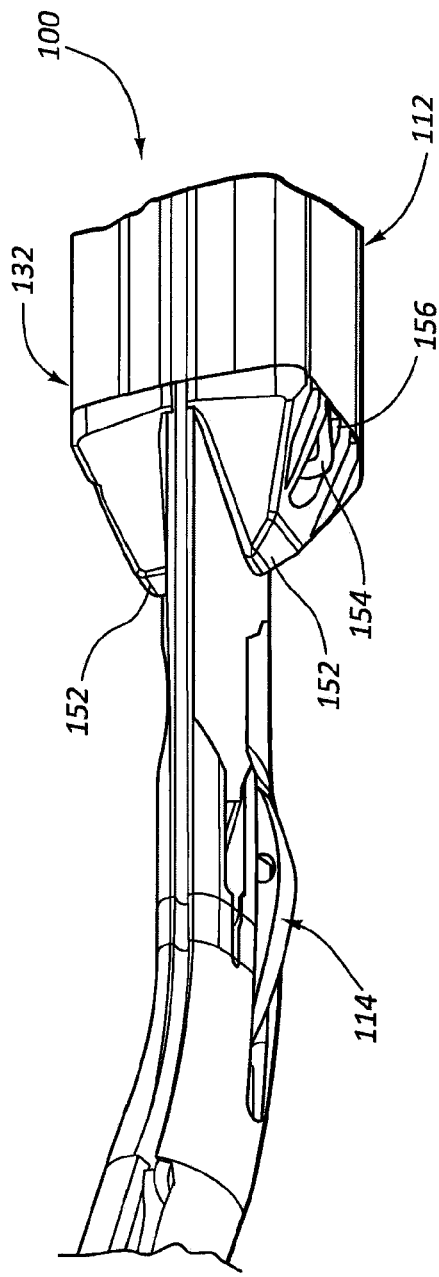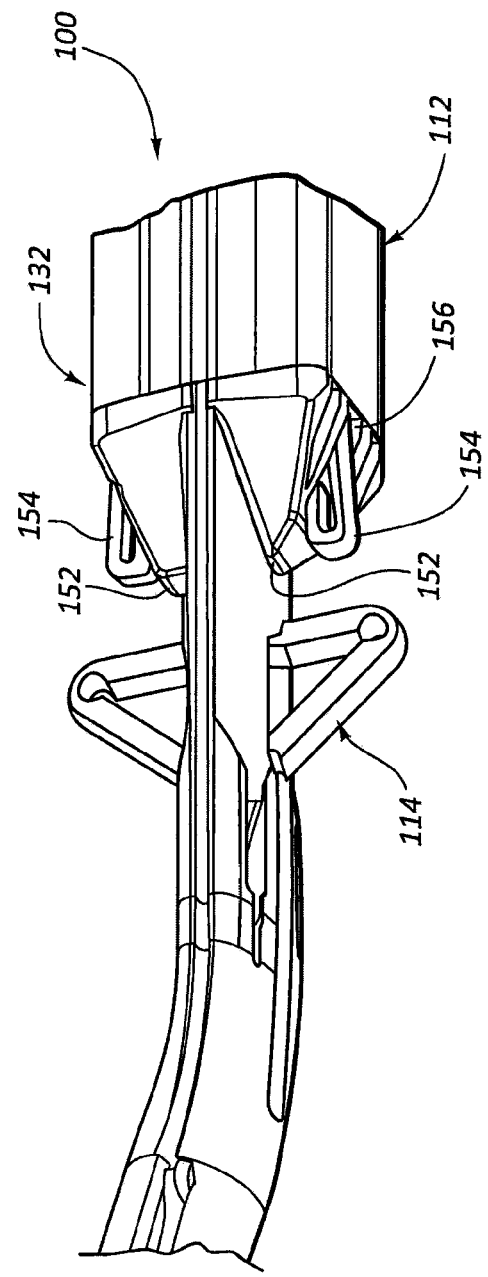
FIG. 14A
FIG. 14B

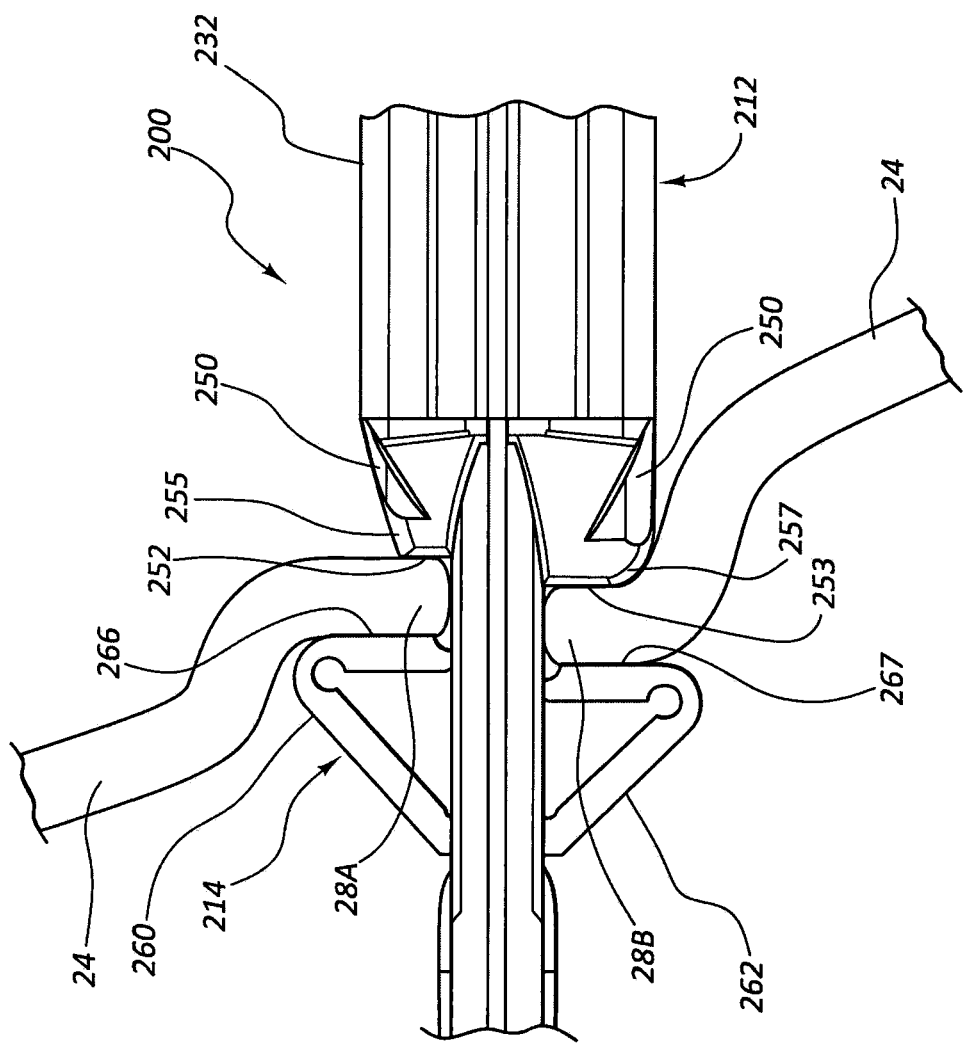

LARGE BORE CLOSURE DEVICE AND METHODS

RELATED APPLICATION

This claims the benefit of U.S. Provisional App. No. 61/494,345, filed 7 Jun. 2011, which is hereby incorporated by reference herein in its entirety.

TECHNICAL FIELD

The present disclosure relates to closure devices, and more specifically relates to closure devices that place sutures across an opening in a vessel wall.

BACKGROUND

Various medical procedures, particularly cardiology procedures, involve accessing a corporeal vessel through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

A number of prior vascular closure devices have been developed in attempting to provide a solution for the problem of closing a hole in the vessel wall. Tissue approximation typically involves passing a length suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. No. 5,643,292 and U.S. Pat. No. 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use.

There remains a need, therefore, to provide a suturing apparatus that is relatively simple in construction, is easy to use, and can effectively approximate tissue surrounding an opening in a vessel wall. There is further a need to provide a suturing device that minimizes the invasiveness of the suturing procedure.

SUMMARY

One aspect of the present disclosure relates to a vascular closure system that includes a body portion, an anchor, a suture carrying portion, and a plurality of needles. The body portion has a distal end surface. The anchor is positionable through a vessel puncture in a vessel wall of a vessel. The anchor defines a vessel contact surface when in an expanded position, wherein withdrawal of the anchor proximally when in the expanded position captures a portion of the vessel wall between the vessel contact surface and the distal end surface to orient the portion of the vessel wall. The suture carrying portion is positionable through the vessel puncture and carries at least one suture member. The plurality of needles extend through the portion of the vessel wall adjacent to the vessel puncture and are configured to connect to the at least one suture member. Withdrawal of the plurality of needles through the portion of the vessel wall positions the at least one suture member through the portion of the vessel wall.

The plurality of needles may be arranged non-perpendicular to a longitudinal axis of the vessel. The body portion may be arranged at an angle relative to the vessel wall prior to capturing a portion of the vessel wall between the vessel contact surface and the distal end surface. The plurality of needles may connect to the at least one suture member with at least one suture connector mounted to the at least one suture member.

The vascular closure system may further include a handle positioned at a proximal end of the body portion, and first and second actuators mounted to the handle. The first actuator may be operable to expand and retract the anchor within the vessel, and the second actuator may be operable to advance and withdraw the plurality of needles.

The plurality of needles may include two pairs of needles, and the at least one suture member may include a pair of suture members. One of the needles may connect to one of the suture members. The body portion may be continuous with the suture carrying portion, and the anchor may expand radially outward from the suture carrying portion. The portion of the vessel wall may be arranged perpendicular to the plurality of needles at any angled arrangement of the body portion relative to a longitudinal axis of the vessel.

Another aspect of the present disclosure relates to a vascular closure device that includes a body portion, an expandable anchor, first and second suture members, and first and second pairs of needles. The body portion is positioned outside a vessel and arranged at an angle relative to a longitudinal axis of the vessel. The expandable anchor is positionable through a puncture in the vessel and operable to capture a portion of the vessel between the body portion and the anchor and arrange the portion of the vessel at an angle relative to a length dimension of the body portion. The first and second suture members are positionable within the vessel. The first and second pairs of needles are operable to advance through the portion of the vessel adjacent to the puncture, connect to the first and second suture members, and be withdrawn through the portion of the vessel to position the first and second suture members through the portion of the vessel.

The vascular closure device may further include a suture carrying portion configured to retain the first and second suture members at a location distal of the anchor. The anchor may be movable between a retracted position within the body portion and an expanded position distal of the body portion. The expandable anchor may be operable to arrange the portion of the vessel at a perpendicular angle relative to the length dimension of the body portion. The body portion may include a handle and first and second actuators, wherein the first actuator is operable to move the anchor between retracted and expanded positions, and the second actuator is operable to move the plurality of needles between withdrawn and advanced positions.

A further aspect of the present disclosure is directed to a method of closing a vascular opening in a vessel wall. The method includes providing a vascular closure device having a body portion, an expandable anchor, a suture carrying portion, and a plurality of needles, wherein the suture carrying portion includes at least one length of suture. The method further includes inserting the anchor and suture carrying portion through the vascular opening, operating the anchor into an expanded position, capturing a portion of the vessel wall between the anchor and a distal end of the body portion, and advancing the plurality of needles through the portion of the vessel wall adjacent to the vascular opening at an angle relative to the vessel wall. The method also includes connecting the plurality of needles to the at least one length of suture, withdrawing the plurality of needles to pull the at least one length of suture through the vessel wall adjacent to the vascular opening, operating the anchor into a retracted position, and removing the anchor and suture carrying portion from the vascular opening.

The method may further include arranging the body portion at a non-perpendicular angle relative to the vessel wall before capturing the vessel wall. Capturing the vessel wall may include arranging a portion of the vessel wall that is captured at a perpendicular angle relative to a longitudinal axis of the body portion for any angled position of the body portion relative to a remaining portion of the vessel wall. The body portion may include a handle and first and second actuators mounted to the handle, and the method may include operating the first actuator to operate the anchor into expanded and retracted positions, and operating the second actuator to advance and withdraw the plurality of needles.

The plurality of needles may include first and second pairs of needles, and the at least one length of suture includes first and second lengths of suture. The step of connecting the plurality of needles to the at least one length of suture may include connecting the first pair of needles to opposing ends of the first length of suture, and connecting the second pair of needles to opposing ends of the second length of suture. Withdrawing the plurality of needles to pull the at least one length of suture through the vessel wall may include pulling lengths of suture through four separate holes in the vessel wall formed by the plurality of needles.

Another aspect of the present disclosure relates to a method of operating a vascular closure device. The method includes providing the vascular closure device with a body portion, an expandable anchor, a suture carrying portion, and a plurality of needles. The suture carrying portion includes at least one suture and being positioned distal of the anchor. The method also includes moving the anchor into an expanded position, moving the anchor proximally toward the body portion when in the expanded position, advancing the plurality of needles from the body portion into contact with the suture carrying portion to connect with the at least one suture, withdrawing the plurality of needles to move the at least one suture proximally into the body portion, moving the anchor distally while in the expanded position, and moving the anchor into a retracted position.

The foregoing and other features, utilities, and advantages of the invention will be apparent from the following detailed description of the invention with reference to the accompanying drawings.

BRIEF DESCRIPTION OF THE DRAWINGS

FIG. 3 is a side cross-sectional view of the vascular closure system of FIG. 2.

FIG. 4 is side cross-sectional view of the vascular closure system of FIG. 1 taken along cross-section indicators 4-4.

FIG. 5A is a perspective view of a distal end portion of the vascular closure system of FIG. 1 extending through a vessel puncture.

FIG. 5B is a side view of a handle portion of the vascular closure system of FIG. 1 with actuator positions representing a state of the distal end portion shown in FIG. 5A.

FIG. 9A is a perspective view of the distal end portion of the vascular closure system of FIG. 8A with the needles connected to sutures within the vessel.

FIG. 9B is a detailed inset showing connection of the needles to the sutures in FIG. 9A.

FIG. 10A is a perspective view of the distal end portion of the vascular closure system of FIG. 9A with the needles retracted partially.

FIG. 10B shows actuator positions of the handle portion representing a state of the distal end portion shown in FIG. 10A.

FIG. 14A is a perspective view of a distal end portion of another example vascular closure system in accordance with the present disclosure.

FIG. 14B is a perspective view of the vascular closure system of FIG. 14A with an anchor and retractable wire form deployed.

FIG. 15C is a side view of the vascular closure system of FIG. 15B with a portion of vessel wall captured.

DETAILED DESCRIPTION

Figure 1:
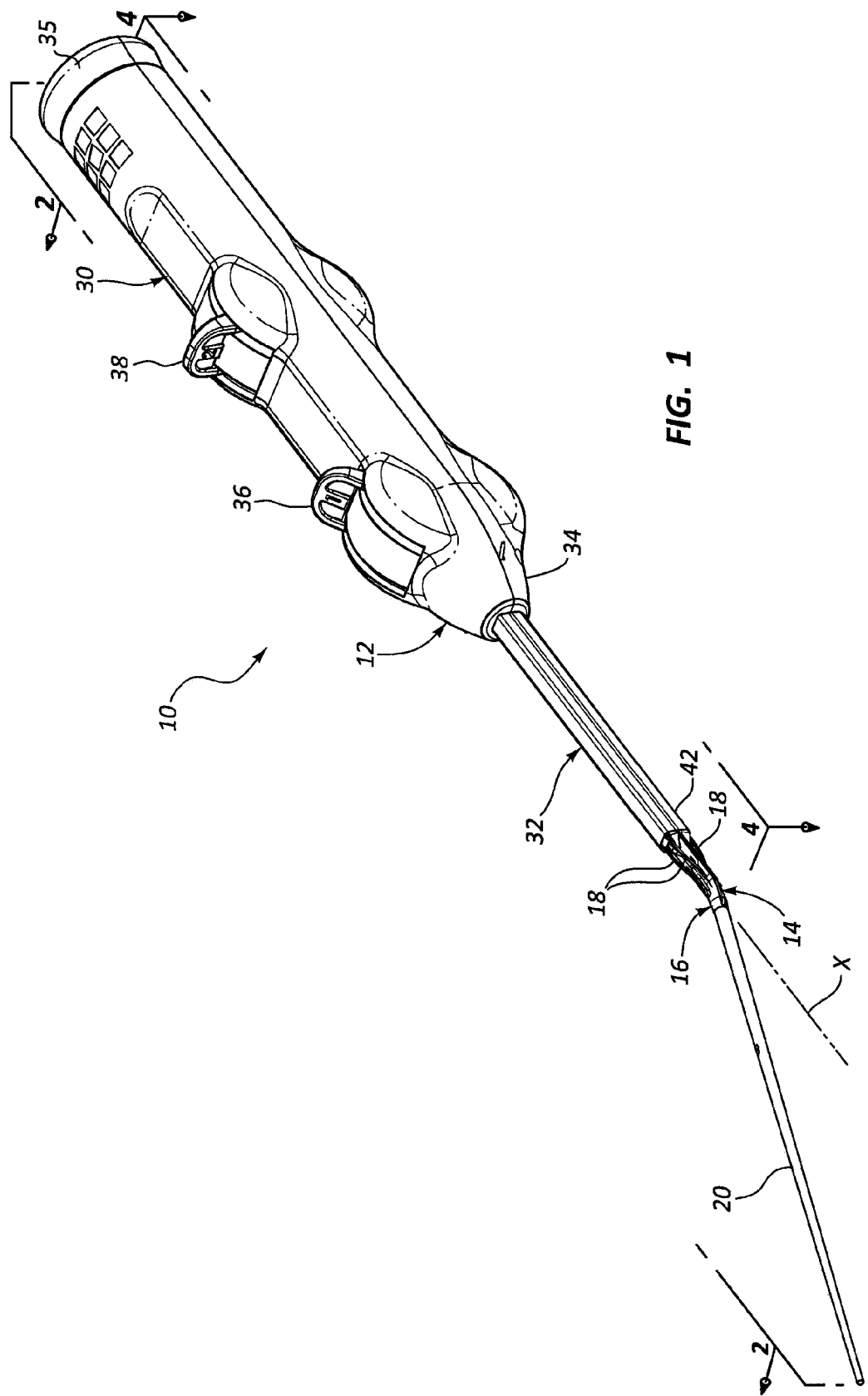
FIG. 1 is a perspective view of an example vascular closure system in accordance with the present disclosure.

The present disclosure is directed to a device that places at least one suture across a wound (e.g., a puncture in a vessel). In one embodiment, the device is adapted and configured to place a pair of sutures across an opening in a wall of a vessel. The present disclosure contemplates that a medical procedure will be performed through a sheath that is inserted through the opening in the vessel wall. The sheath provides access to the inside of the vessel. The device may be used prior to the sheath being inserted through the opening or after the medical procedure has been completed and the sheath removed. The device deploys at least one suture across the vessel opening by inserting a plurality of needles through the vessel wall adjacent to the opening. The needles grasp lengths of suture held by the device within the vessel, and withdrawing the needles pulls the lengths of suture through the vessel wall. The sutures may be subsequently used to close the opening. One use of the device is to place at least one suture through the vessel wall, wherein the suture is later used to close a puncture in the vessel wall (e.g., a puncture in a femoral artery incurred during a catheter based procedure).

Referring now to FIGS. 1-4, an example vascular closure system 10 is shown including a body portion 12, an anchor 14, a suture carrying portion 16, a plurality of needles 18, and a distal locator tip 20. The body portion 12 may include a handle 30 and a delivery portion 32. The anchor 14 may be expandable and retractable relative to the body portion 12 and suture carrying portion 16. The needles 18 are operable to move between withdrawn positions within the body portion 12, and extended positions protruding through a vessel wall. The needles may be used to grasp lengths of suture carried by the suture carrying portion 16 and, when withdrawn, pull the lengths of suture through the vessel wall adjacent to the vessel puncture. Operation of the vascular closure system 10 is shown and described in further detail below related to FIGS. 5A-13.

Figure 2:
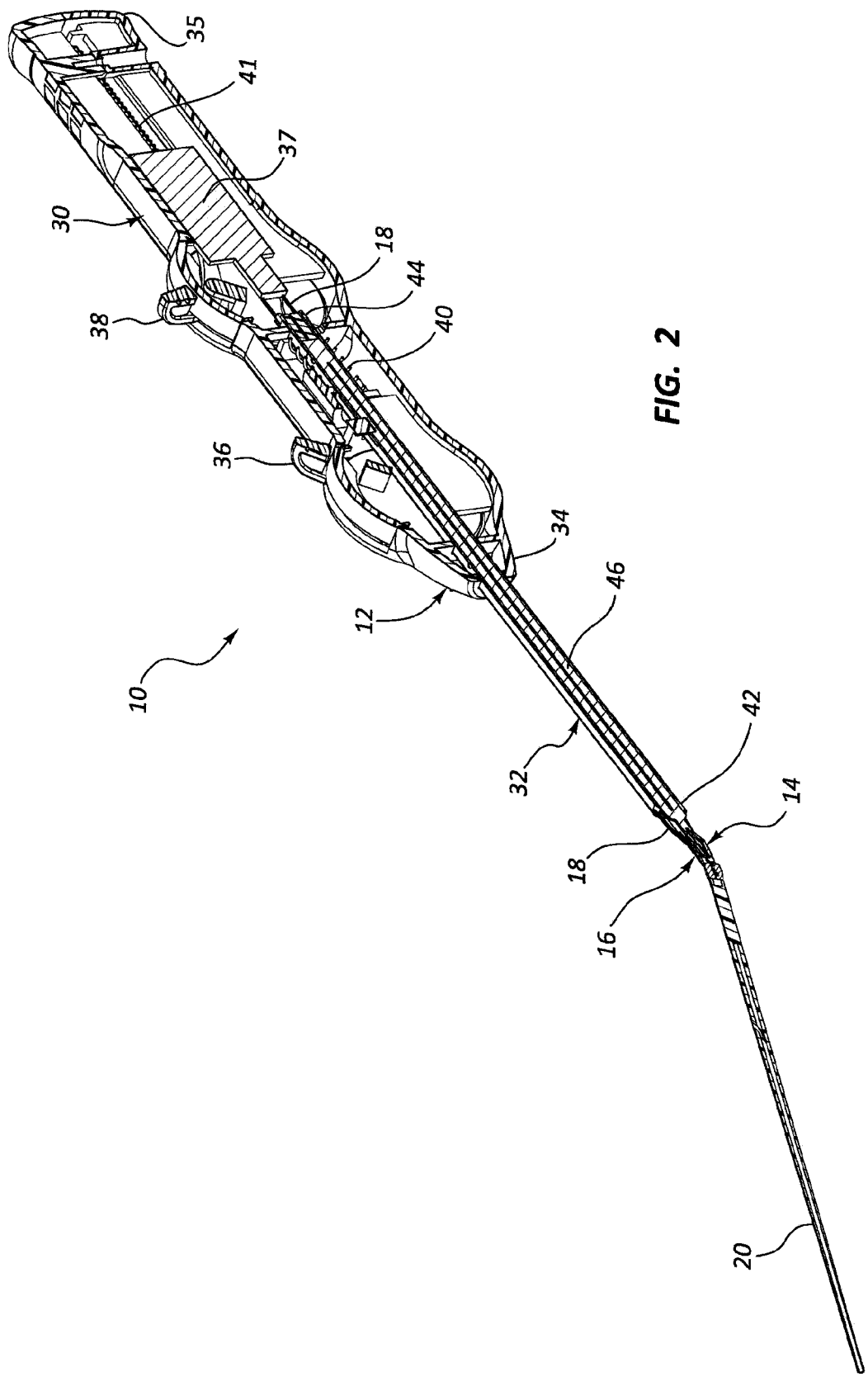
FIG. 2 is a perspective cross-sectional view of the vascular closure system of FIG. 1 taken along cross-section indicators 2-2.

The handle 30 of the body portion 12 includes distal and proximal ends 34, 35, first and second actuators 36, 38, and first and second biasing members 40, 41 (see FIGS. 1 and 2). The first and second actuators 36, 38 may be pivotally mounted to the handle 30. Operation of the first actuator 36 moves the anchor 14 between retracted and extended positions. Typically, the anchor 14 maintains the retracted position while advancing the vascular closure system 10 through a vessel wall. The vascular closure system 10 may have its smallest outer profile when the anchor 14 is in the retracted position to promote insertion through the vessel puncture. The first actuator 36 is rotated forward to expand or extend the anchor 14 into a position that limits removal of the vascular closure system 10 from the vessel (see FIG. 6A).

The anchor 14 may be movable axially relative to the body portion 12 when the anchor 14 is in the expanded position. Operation of the first actuator 36 through a first portion of its actuation path (e.g., through a first portion of its rotation path in a forward or advancing direction) may move the anchor 14 between expanded and retracted positions (see FIGS. 6A-B). Operation of the first actuator 36 through a second portion of its actuation path (e.g., through a second portion of its rotation path in the forward or advancing direction) may move the expanded anchor axially in a rearward direction (e.g., withdraw the expanded anchor 14 proximally toward the body portion 12 as shown in FIGS. 7A-C).

The second actuator 38 is operable to move the needles 18 between withdrawn and extended positions. The needles 18, when in a withdrawn position, may be completely recessed within the body portion 12. Operation of the second actuator 38 (i.e., rotation to a forward rotated position) advances the needles 18 distally out of the body portion 12 and through a vessel wall (see FIGS. 8A-B). The needles 18 include distal needle tips 19 (see FIGS. 8A and 9A-B) that connect to first and second sutures 82, 84 carried by the suture carrying portion 16 (see FIGS. 9A-B). Once the needles 18 are connected to the first and second sutures 82, 84, the second actuator 38 is operated to withdraw the needles 18 back into the body portion 12 (see FIGS. 10A-B). Repositioning the needles 18 proximally pulls the sutures through the vessel wall. Removing the vascular closure system 10 from the vessel exposes the sutures for handling by the operator outside of the patient.

Referring to FIGS. 2 and 3, the body portion 12 may include first and second biasing members 40, 41 and other mechanical features that provide operation of the first and second actuators 36, 38. The first and second biasing members 40, 41 may bias the first and second actuators 36, 38, respectively, into certain articulated or rotated positions (e.g., to a rearward rotated position). In one example, the handle 30 includes a needle carrier 37 to which the plurality of needles 18 are mounted at their proximal end (see FIGS. 2 and 3). Actuating the second actuator 38 may advance and withdraw the needle carrier 37 within the handle 30 and relative to the delivery portion 32 of the body portion 12.

As shown in FIG. 4, the delivery portion 32 of the body portion 12 includes distal and proximal ends 42, 44, respectively, a hollow interior 46, an anchor opening 48, a plurality of needle openings 50 (FIG. 5A) at the distal end 42, and a distal end surface 52. The proximal end 44 of the delivery portion 32 is mounted to the handle 30. The suture carrying portion 16 extends from the distal end 42 of the delivery portion 32. As shown in FIG. 3, portions of the anchor 14, needles 18, and first and second actuators 36, 38 may be mounted within the hollow interior 46 of the delivery portion 32. Portions of the anchor 14 may extend through the anchor opening 48 when the anchor 14 moves between retracted and expanded positions. The needles may advance and withdraw through the needle openings 50.

The distal end surface 52 may define a contact surface against which a portion of the vessel contacts when captured between the body portion 12 and anchor 14. The distal end surface 52 (FIG. 5A) may include a generally flat or planar portion that extends generally perpendicular to a longitudinal axis X of the body portion 12 (see FIG. 3). A surface area of the distal end surface 52 may be enhanced by stop features that appear when the anchor 14 is moved into the expanded position. FIGS. 14A and 14B illustrate an alternative vascular closure device 100 that includes a body portion 112 and anchor 114. The body portion 112 includes a delivery portion having a distal end that is tapered to improve ease of insertion of the body portion 112 through a vessel puncture. A leading distal end surface 152 is relatively low profile until the anchor 114 is deployed. A retractable wire form 154 moves distally out of a wire form recess 156 when the anchor 114 is deployed to increase a surface area of the distal end surface 152 of the body portion 112. An increased surface area for the distal end surface 152 may assist in capturing and holding the vessel wall while penetrating the vessel wall with needles 18. The retractable wire form 154 or other feature that selectively increases a size of the distal end surface 152 may be added to the vascular closure system 10.

The anchor 14 is moveable between a retracted position (see FIGS. 1-5A) and an expanded or extended position (see FIGS. 7A and 7C). While in the retracted position, the vascular closure system 10 has a reduced profile that permits insertion of the anchor 14 through a tissue puncture. Upon actuation into an expanded or extended position, the anchor 14 resists removal of the vascular closure system 10 back through the tissue puncture.

The anchor 14 includes first and second arms 60, 62, a bend portion 64, and a proximal surface 66. In some arrangements, the first and second arms 60, 62 include more than one bend portion 64, and may have any desired shape or size when in the expanded position. The proximal surface 66 may be arranged generally perpendicular to a longitudinal axis of the vascular closure system (e.g., the longitudinal axis X of the body portion 12 shown in FIG. 7C).

The anchor 14, when in the expanded position shown in FIGS. 6A-7C, may be repositioned proximally to capture a portion of a vessel wall 24 between the proximal surface 66 of the anchor 14 and the distal end surface 52 of the body portion 12. The anchor 14 may be moveable axially while the anchor 14 maintains an expanded position. In some arrangements, the anchor 14 moves into the expanded position while at the same time being repositioned proximally to capture the vessel wall 24 between the anchor 14 and body portion 12. The vessel wall 24 may be released by advancing the anchor 14 distally away from the body portion 12. In some arrangements, the anchor 14 may move into a retracted (unexpanded) orientation concurrently with advancing the anchor 14 distally to release the vessel wall 24.

The anchor 14 may be configured to provide a maximum surface area at the proximal surface 66 when the anchor 14 is in the expanded position. In some arrangements, the anchor 14 includes only a single arm, while in other arrangements the anchor 14 includes three or more arms that define the proximal surface 66. In one example, the anchor 14 extends distally out of the body portion 12, while in other arrangements at least a portion of the anchor 14 extends radially outward from the suture carrying portion 16 or other structure that is positioned distal of the body portion 12.

The suture carrying portion 16 includes distal and proximal ends 70, 72, an anchor slot 74, a plurality of needle receiver recesses 76, a plurality of suture recesses 78, a plurality of suture connectors 80, and first and second sutures 82, 84. The suture carrying portion 16 is connected to the delivery portion 32 of the body portion 12 at the proximal end 72. The distal locator tip 20 extends distally from the distal end 70 of the suture carrying portion 16.

The anchor slot 74 may extend distally from the distal end surface 52 of the body portion 12. The anchor slot 74 may be continuous with the anchor opening 48 of the delivery portion 32.

The needle receiver recesses 76 may be constructed as grooves or recesses along a length dimension of the suture carrying portion 16. Tips of the needles 18 may extend into the needle receiver recesses 76 to guide the needles 18 into the suture connectors 80.

Figure 13:
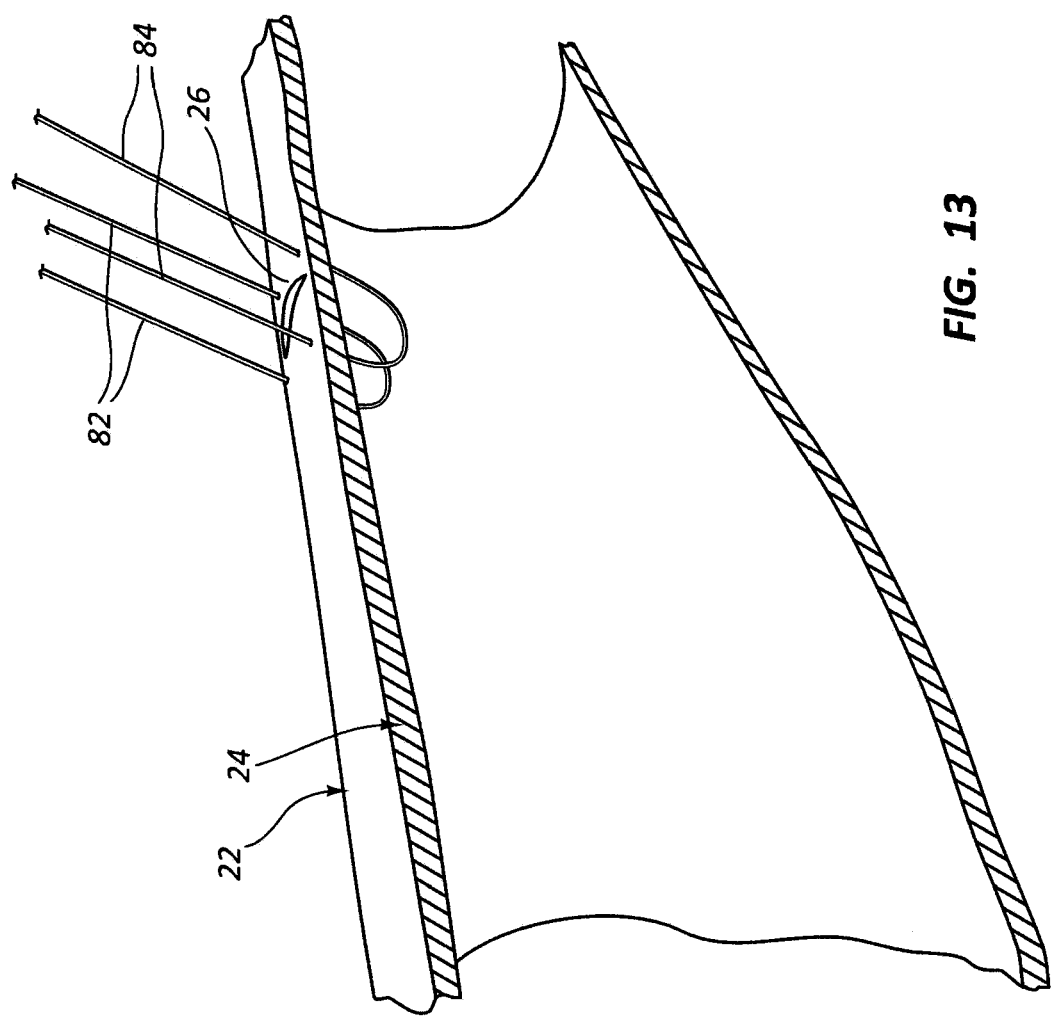
FIG. 13 illustrates the sutures extending across the vascular puncture upon removal of the vascular closure system.

The vessel 22 includes a puncture 26 formed in the vessel wall 24. The needles 18 form a plurality of needle openings 29 positioned adjacent to the puncture 26. The needle openings 29 may be positioned radially outward and spaced apart from the puncture 26. Typically, the puncture 26 is generally elongate having opposing sides that define a length of the puncture and opposing ends. The first and second sutures 82, 84 may extend across the puncture 26 from one side to an opposing side as shown in FIG. 13.

The first and second sutures 82, 84 extend through the suture recesses 78 and are coupled to the suture connectors 80. The suture connectors 80 may be connected at opposing ends of the first and second sutures 82, 84. Connecting the suture connectors 80 to the needles 18 couples the first and second sutures 82, 84 to the needles 18. Typically, a separate needle 18 is connected to a separate end of one of the first and second sutures 82, 84.

The first and second sutures 82, 84 may extend at least partially within the needle receiver recesses 76 and the suture recesses 78. Additional length of the first and second sutures 82, 84 may extend along the suture carrying portion 16 proximally and extend into the body portion 12 as shown in at least FIG. 5A.

Upon connection of the needles 18 to the suture connectors 80, the needles 18 may be withdrawn proximally to pull the first and second sutures 82, 84 through the vessel wall 24 at a location adjacent to a puncture 26.

The suture connectors 80 may include a wire loop at one end for connection to a needle 18, and have a suture connection feature at an opposing end for connection to one of the first and second sutures 82, 84. Many other constructions and configurations are possible for the suture connectors 80 to provide a connection, either releasable or permanent, between the needles 18 and the first and second sutures 82, 84.

Figure 11:
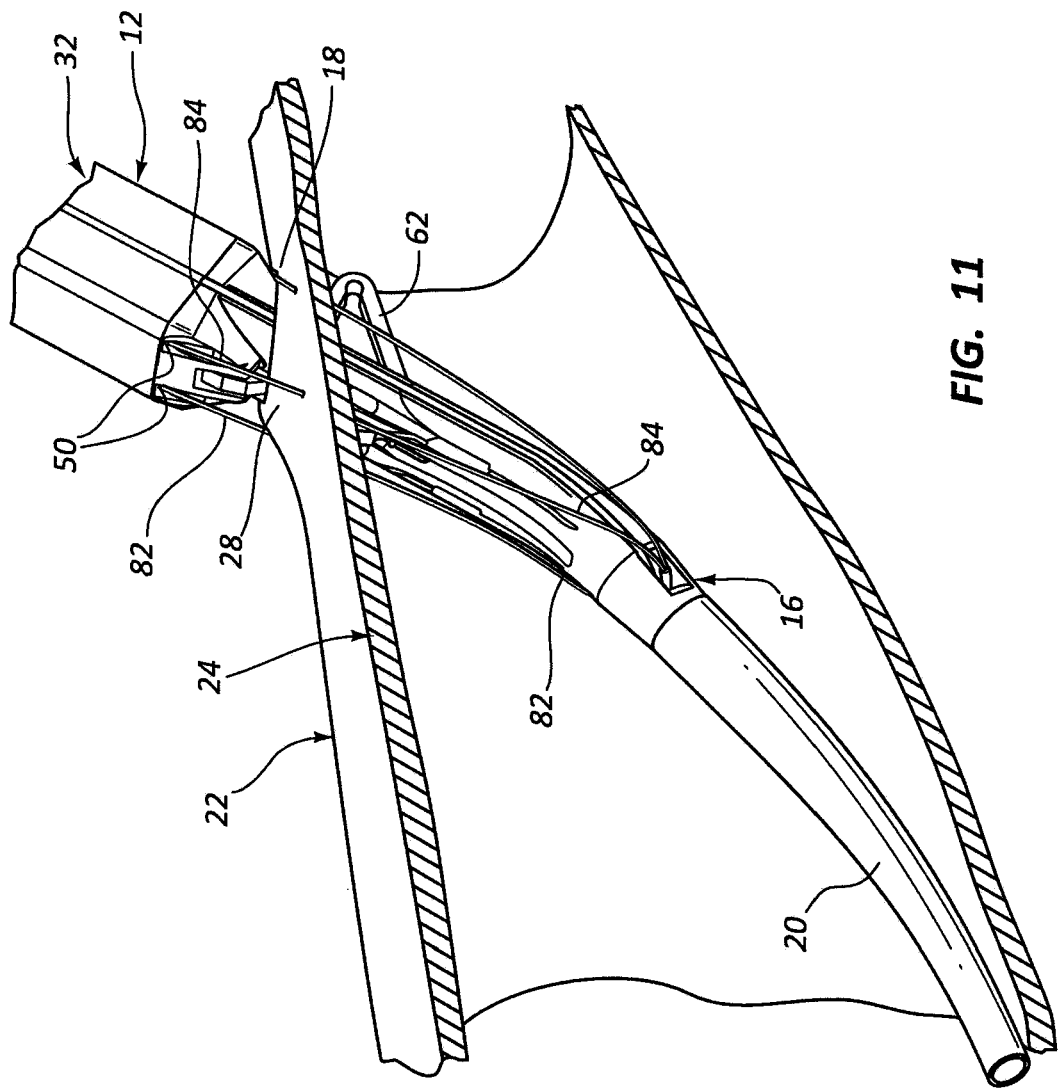
FIG. 11 is a perspective view of the distal end portion of the vascular closure system of FIG. 10A with the needles fully withdrawn and the sutures extending through the vessel wall.
Figures 12A, 12B:
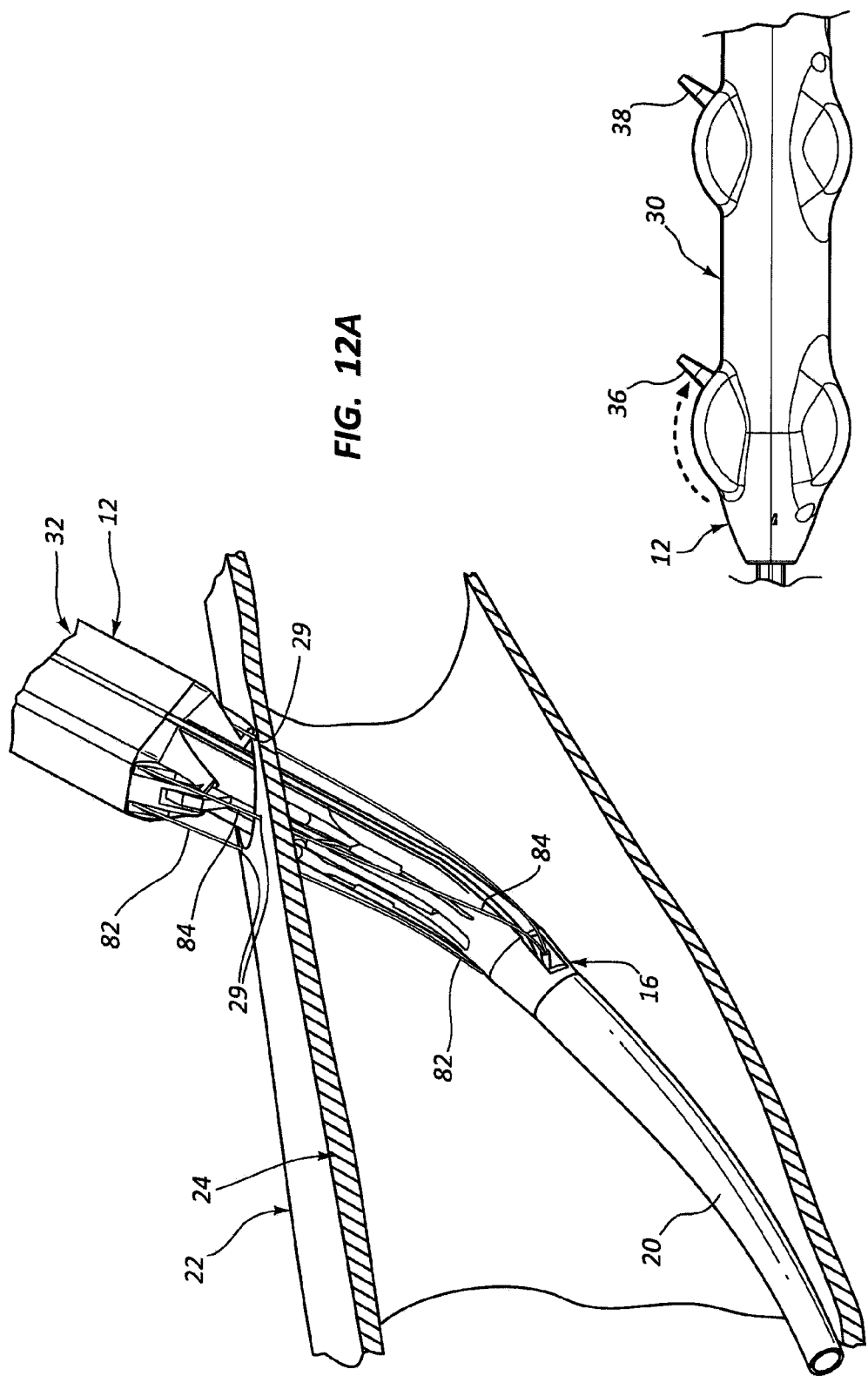
FIG. 12A is a perspective view of the distal end portion of the vascular closure system of FIG. 11 with the anchor in a retracted position.
FIG. 12B shows the actuator positions of the handle portion representing a state of the distal end portion shown in FIG. 12A.

The needles 18 include a distal needle tip 19. When the needles 18 are advanced by activation of the second actuator 38, the distal needle tips 19 extend through the vessel wall 24 and into the needle receiver recesses 76 (see FIG. 8A). Further advancing the needles 18 connects the distal needle tips 19 with the suture connectors 80 as shown in FIG. 9A. Withdrawing the needles 18 proximally by actuation of the second actuator 38 draws the first and second sutures 82, 84 through the needle openings 29 in the vessel wall 24 as shown in FIGS. 10A and 11. Withdrawing the vascular closure system 10 places the first and second sutures 82, 84 across a puncture 26 as shown in FIG. 13.

Figure 6A:
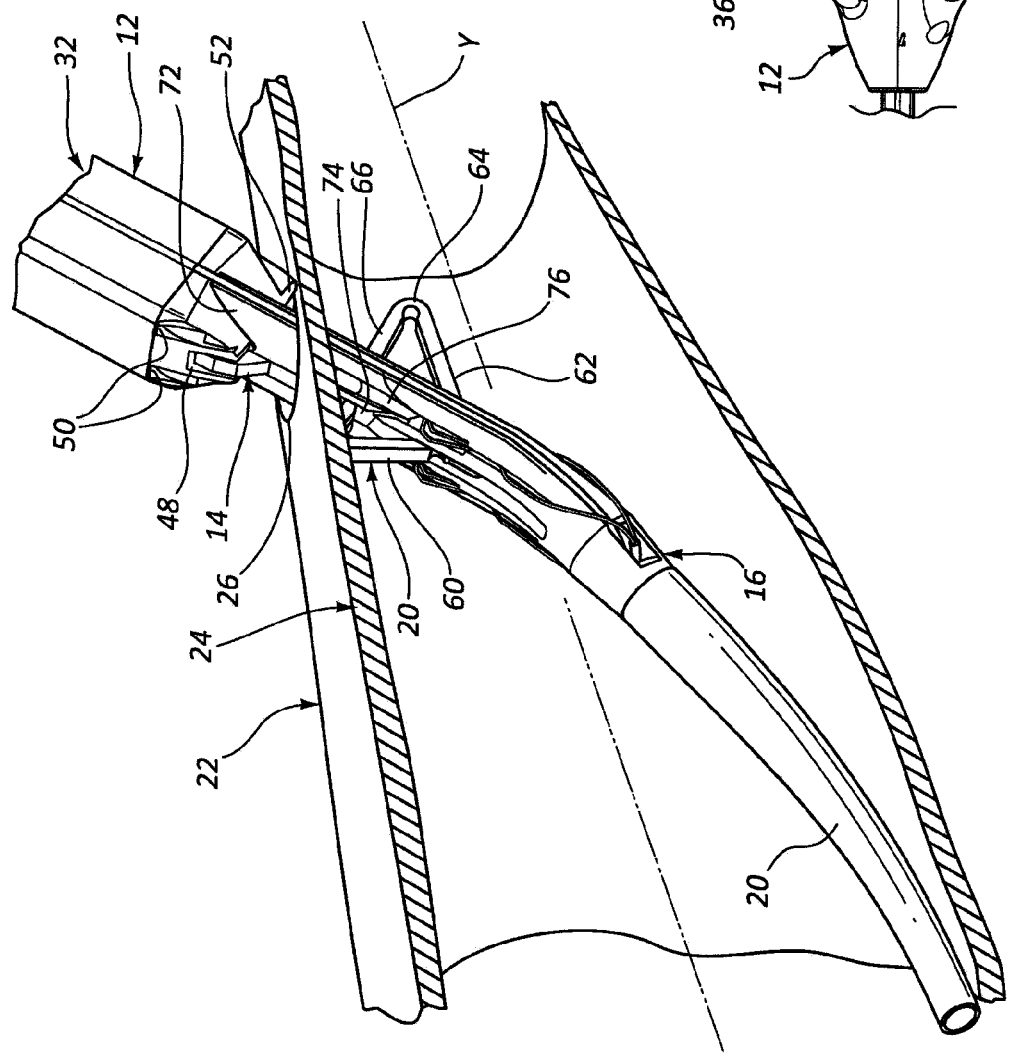
FIG. 6A is a perspective view of the distal end portion of the vascular closure system of FIG. 5A with an anchor in an extended position.
Figure 6B:
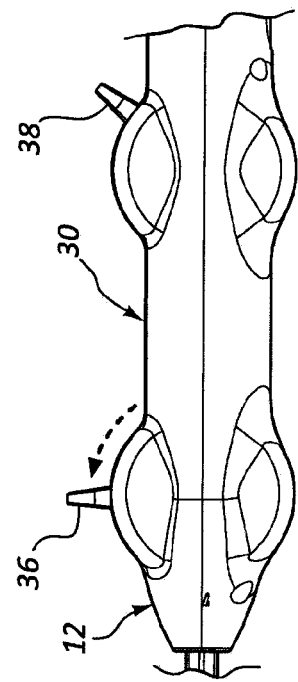
FIG. 6B shows actuator positions of the handle portion representing a state of the distal end portion shown in FIG. 6A.
Figure 7C:
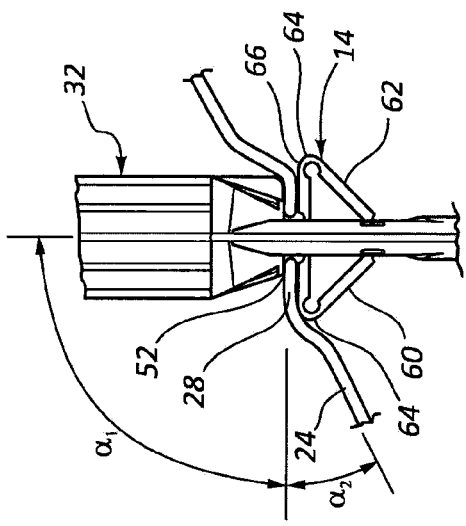
FIG. 7C is a side view of the distal end portion of the vascular closure system of FIG. 7A.
Figure 7B:
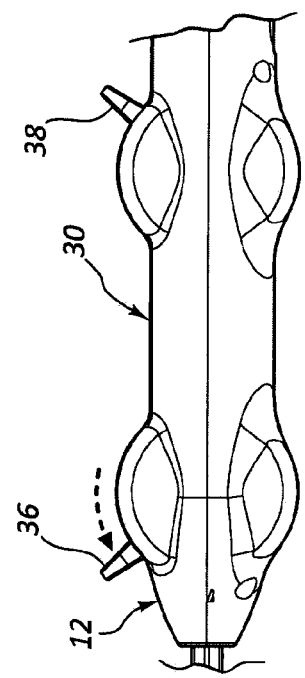
FIG. 7B shows actuator positions of the handle portion representing a state of the distal end portion shown in FIG. 7A.
Figure 7A:
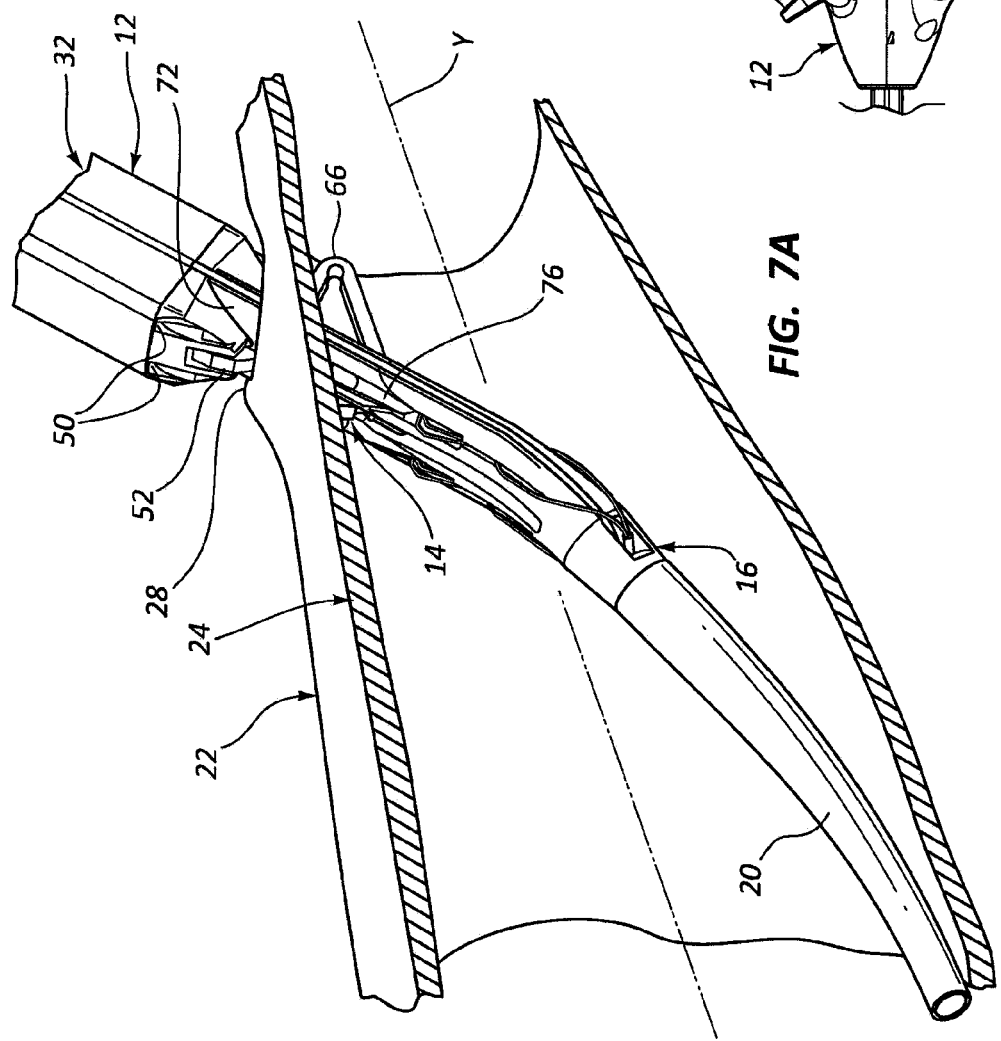
FIG. 7A is a perspective view of the distal end portion of the vascular closure system of FIG. 6A with a portion of the vessel wall captured between the anchor and a body portion of the vascular closure system.
Figure 8A:
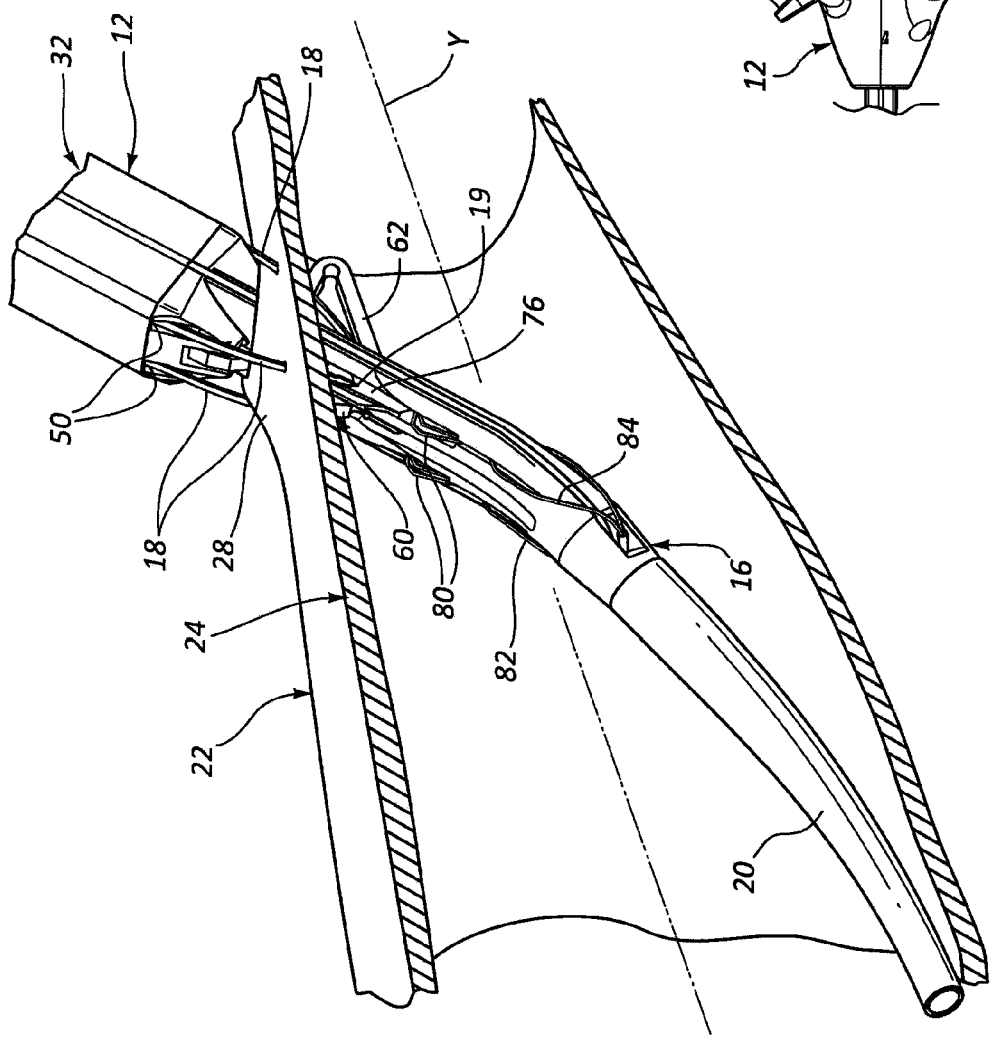
FIG. 8A is a perspective view of the distal end portion of the vascular closure system of FIG. 7A with needles extending through the vessel wall.
Figure 8B:
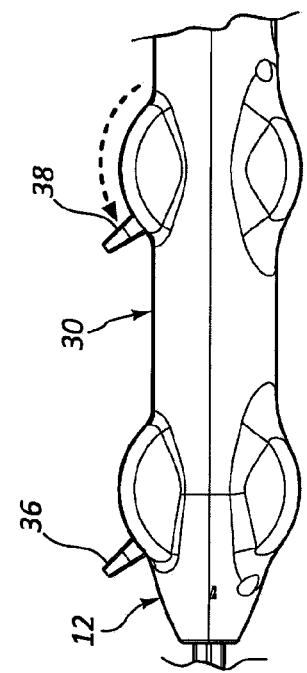
FIG. 8B shows actuator positions of the handle portion representing a state of the distal end portion shown in FIG. 8A.

A vessel wall aligned portion 28 may be that portion of the vessel wall 24 that is captured between the proximal surface 66 of the anchor 14 and the distal end surface 52 of the body portion 12 (e.g., see FIGS. 6A and 7C). The body portion 12 is typically inserted through the vessel wall 24 at an angle (shown as a combined angle $\alpha_1 + \alpha_2$ in FIG. 7C) relative to an outer surface of the vessel wall 24 or a longitudinal axis Y of the vessel 22 as shown in FIGS. 7A and 7C. When the expanded anchor 14 is moved proximally, the vessel wall aligned portion 28 is captured and moved into an orientation that is at an angle $\alpha_2$ relative to the remaining portions of the vessel wall 24 (see FIG. 7C). The vessel wall aligned portion 28 is arranged at a perpendicular angle $\alpha_1$ relative to the longitudinal axis X of the body portion 12.

As the needles 18 are advanced by actuation of the second actuator 38, the needles 18 protrude at a perpendicular angle relative to the vessel wall aligned portion 28. The needles 18 are shown in at least FIG. 8A arranged at a non-perpendicular angle relative to the remaining portions of the vessel wall 24. Typically, the body portion 12 is inserted at an angle $\alpha_1 + \alpha_2$ that is greater than 90°, and preferably in the range of about 100° to about 150 degrees. In some arrangements, the angle $\alpha_1 + \alpha_2$ is about 90° so that the vessel wall 24 and vessel wall aligned portion 28 are arranged generally in parallel.

Providing the vessel wall aligned portion 28 perpendicular to the angle of advancing the needles 18 permits advancement of the needles 18 through the vessel wall concurrently and at a more precise and consistent spacing from the puncture 26 regardless of the angle $\alpha_1 + \alpha_2$. The improved consistency in spacing of the needle openings 29 defined by the needles 18 relative to the puncture 26 may provide improved closing and hemostasis of the puncture 26 using the first and second sutures 82, 84 that are placed through the needle openings 29. Furthermore, the consistent placement of the sutures relative to the puncture may result in less vessel scarring and less stenosis at the site of the vessel puncture.

Figure 15A:
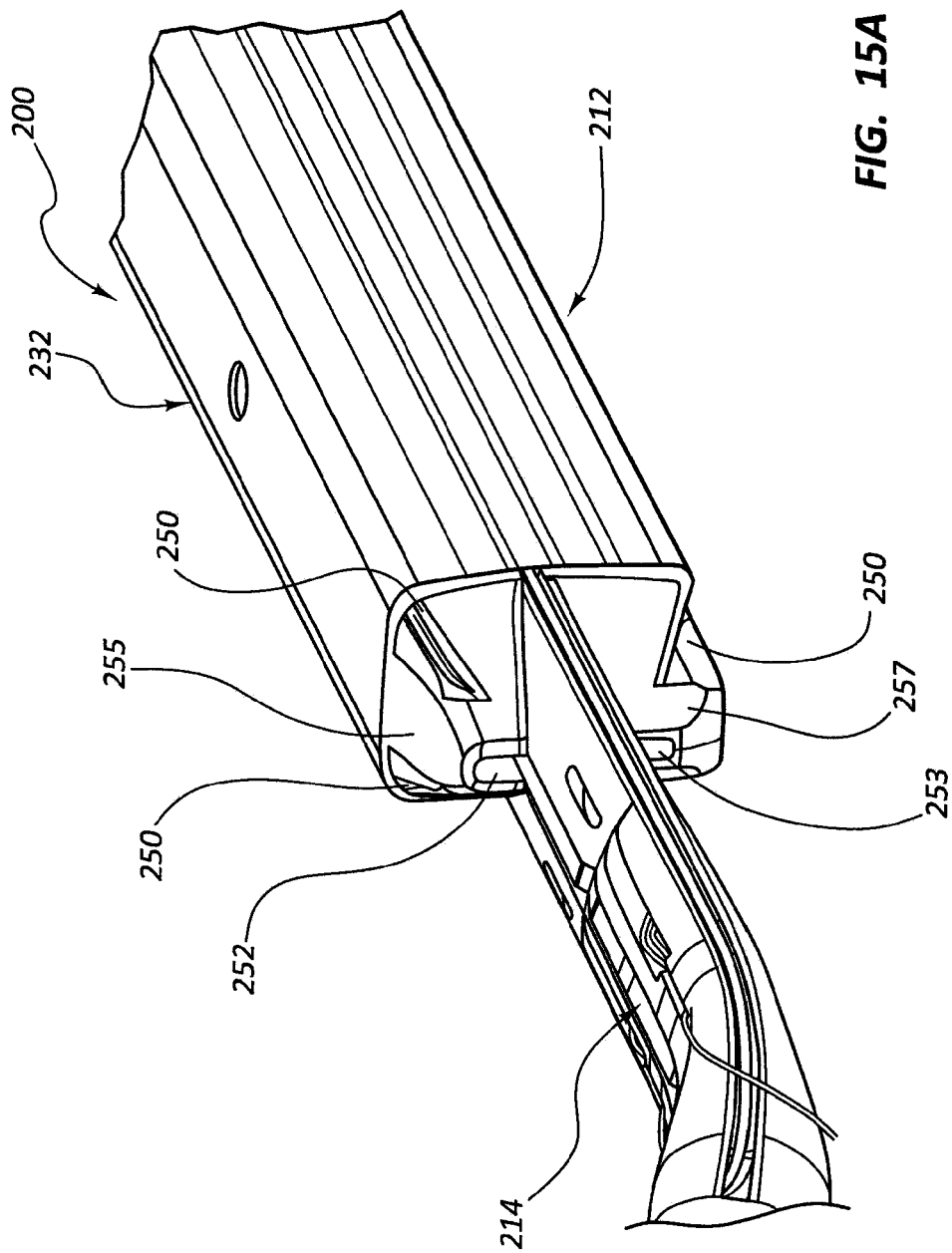
FIG. 15A is a perspective view of a portion of another example vascular closure system in accordance with the present disclosure.
Figure 15B:
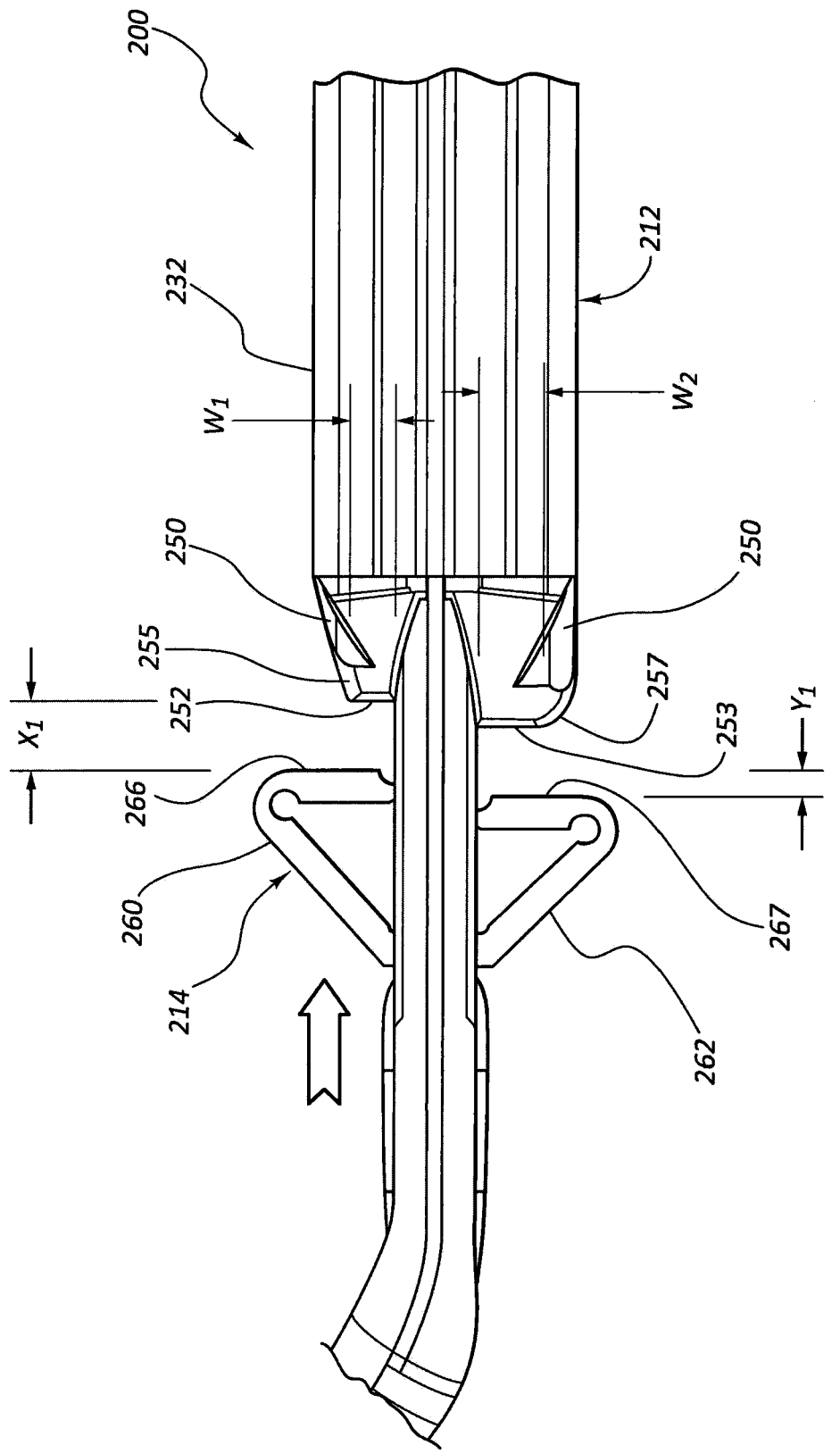
FIG. 15B is a side view of the vascular closure system of FIG. 15A with an anchor in an extended position.

Referring now to FIGS. 15A-C, another example vascular closure system 200 is described. The vascular closure system 200 includes a body portion 212 and an anchor 214. The body portion 212 includes a delivery portion 232 having first and second distal end surfaces 252, 253 defined by front and rear portions 255, 257. The front and rear portions 255, 257 may each have a tapered construction. The tapered construction may include at least one tapered surface that extends proximally from the first and second distal end surfaces 252, 253. The tapered construction of the front and rear portions 255, 257 may improve ease of inserting the body portion 212 through a vessel puncture.

The front and rear portions 255, 257 may be arranged along opposite sides of the delivery portion 232. In at least one arrangement, the front and rear portions 255, 257 are arranged 180° from each other around a circumference of the delivery portion 232. The front portion 255 may be oriented into a rotated position that is positioned further distally along the vessel. The rear portion 257 may be oriented in a rotated position further proximally along the vessel.

The first and second distal end surfaces 252, 253 may be offset axially from each other by a distance $X_1$. The distance $X_1$ may be in the range of, for example, about 0.1 inches to about 0.5 inches, and more specifically about 0.1 inches to about 0.2 inches. The first and second distal end surfaces 252, 253 may be arranged generally perpendicular to a longitudinal axis or length dimension of the body portion 212. At least one needle opening 250 may be defined in each of the front and rear portions 255, 257 and configured for passage of a needle.

The first and second distal end surfaces 252, 253 may have widths, $W_1$, $W_2$, respectively (see FIG. 15B). The widths $W_1$, $W_2$ may have different sizes. In the illustrated example, $W_1$ is less than $W_2$. The widths $W_1$, $W_2$ are typically in the range of about 0.05 inches to about 0.2 inches.

The anchor 214 may include first and second arms 260, 262 that define first and second proximal surface 266, 267, respectively. The first and second arms 260, 262 may be arranged along opposite sides of the delivery portion 232. In at least one arrangement, the first and second arms 260, 262 are arranged 180° from each other around a circumference of the delivery portion 232.

The first and second proximal surfaces 266, 267 may be offset axially from each other a distance $Y_1$. The distance $Y_1$ may be in the range of, for example, about 0.1 inches to about 0.5 inches, and more specifically about 0.1 inches to about 0.2 inches. The first and second proximal surfaces 266, 267 may be arranged generally perpendicular to a longitudinal axis or length dimension of the delivery portion 232.

FIG. 15C shows first and second aligned portions 28A, 28B of the vessel wall 24 captured between the first and second distal end surfaces 252, 253 and the first and second proximal surfaces 266, 267, respectively. The first and second aligned portions 28A, 28B may be arranged at different or offset axial positions relative to the delivery portion 232 of the body portion 212.

Figure 16A:
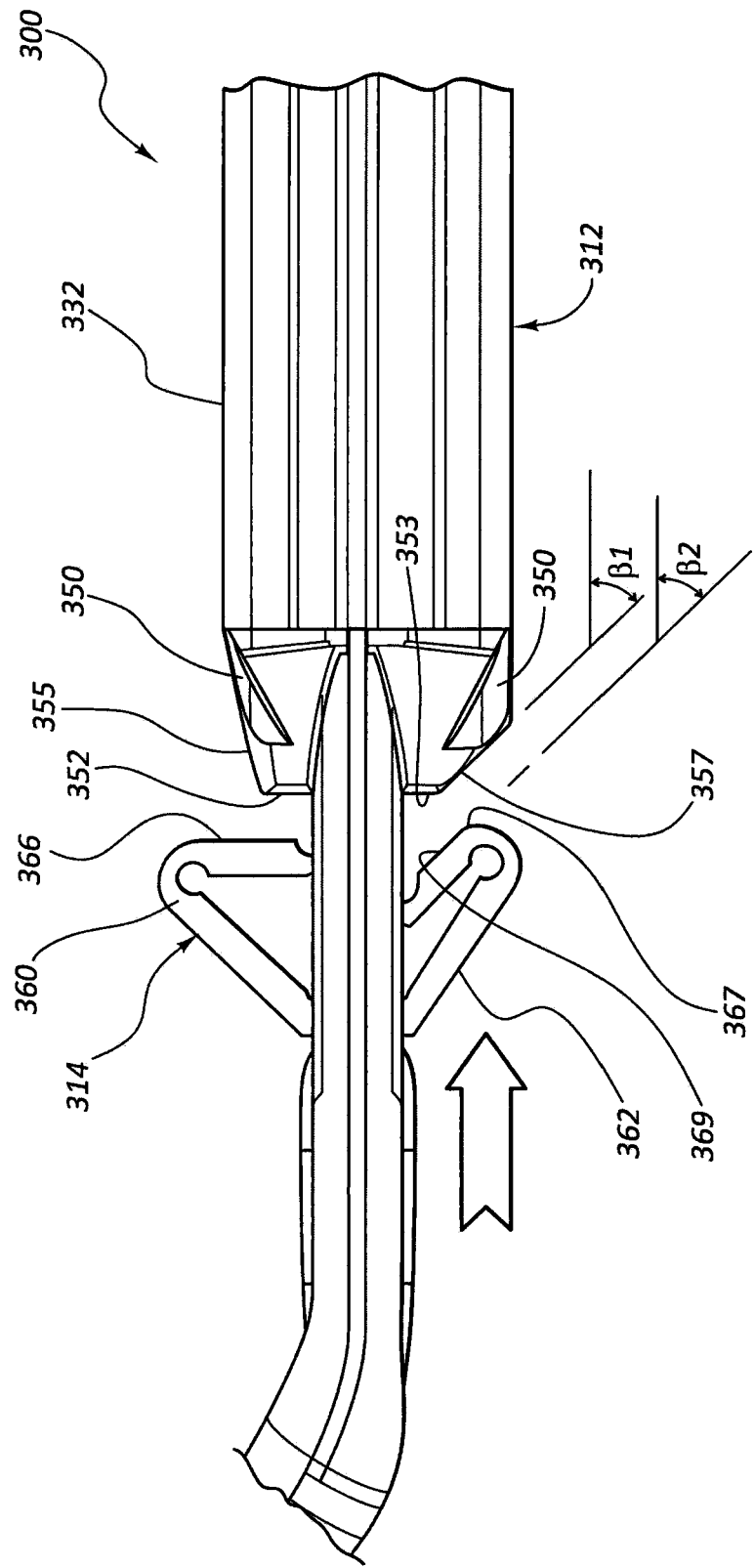
FIG. 16A is a side view of a portion of another example vascular closure system in accordance with the present disclosure.
Figure 16B:
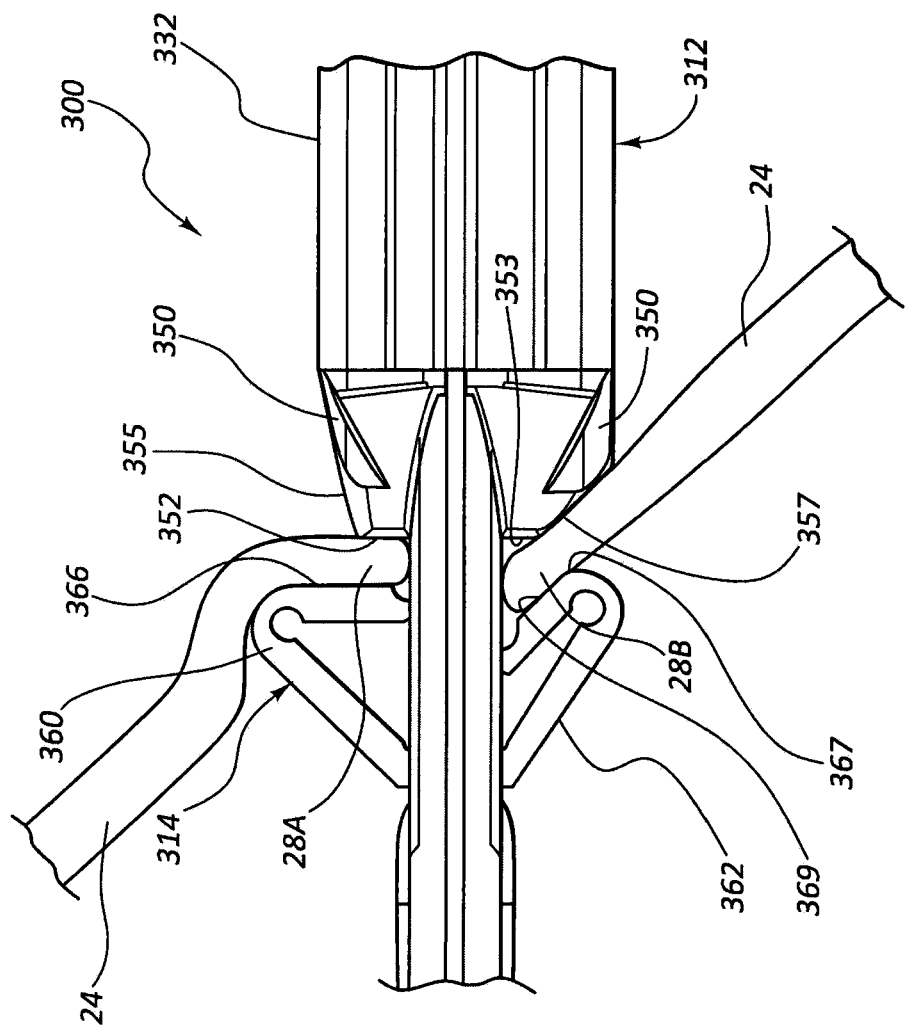
FIG. 16B is a side view of the vascular closure system of FIG. 16B with a portion of vessel wall captured.

Referring now to FIGS. 16A-B, another example vascular closure system 300 is described. The vascular closure system 300 includes a body portion 312 and an anchor 314. The body portion 312 includes a delivery portion 332 having first and second distal end surfaces 352, 353 defined by front and rear portions 355, 357. The front and rear portions 355, 357 may each have a tapered construction. The tapered construction may include at least one tapered surface that extends proximally from the first and second distal end surfaces 352, 353. The tapered construction of the front and rear portions 355, 357 may improve ease of inserting the body portion 312 through a vessel puncture.

The front and rear portions 355, 357 may be arranged along opposite sides of the delivery portion 332. In at least one arrangement, the front and rear portions 355, 357 are arranged 180° from each other around a circumference of the delivery portion 332. The front portion 355 may be oriented in a rotated position further distally along the vessel. The rear portion 357 may be oriented and rotated in a position that is further proximally along the vessel.

The first and second distal end surfaces 352, 353 may have different constructions. For example, the first distal end surface 352 may be arranged generally perpendicular to a longitudinal axis or length dimension of the delivery portion 332. The second distal end surface 353 may include a portion that is arranged at an angle $\beta_1$. The second distal end surface 353 may include a portion that is also arranged generally perpendicular to a longitudinal axis of the delivery portion 332. The angle $\beta_1$ may be in the range of, for example, about 20° to about 70°, and more specifically about 30° to about 60°. In at least some arrangements, the first and second distal end surfaces 352, 353 are arranged offset axially from each other, such as a distance $X_1$ described with reference to vascular closure system 200. At least one needle opening 350 may be defined in each of the front and rear portions 355, 357 and configured for passage of a needle.

The anchor 314 may include first and second arms 360, 362 that define first and second proximal surface 366, 367, respectively. The first and second arms 360, 362 may be arranged along opposite sides of the delivery portion 332. In at least one arrangement, the first and second arms 360, 362 are arranged 180° from each other around a circumference of the delivery portion 332.

The first and second proximal surfaces 366, 367 may have different constructions. For example, the first proximal surface 366 may be arranged generally perpendicular to a longitudinal axis or length dimension of the delivery portion 332. The second proximal surface 367 may include an angled portion 369 that is arranged at an angle $\beta_2$. The angle $\beta_2$ may be in the range of, for example, about 20° to about 70°, and more specifically about 30° to about 60°. In some arrangements, the angles $\beta_1$, $\beta_2$ may be substantially equal to each other.

In at least some arrangements, portions of the first and second proximal surfaces 366, 367 are arranged offset axially from each other, such as a distance $Y_1$ described with reference to vascular closure system 200. In some arrangements, a proximal most portion of the first and second arms 360, 362 may be arranged in parallel at substantially the same axial location along the delivery portion 332.

FIG. 16B shows first and second aligned portions 28A, 28B of the vessel wall 24 captured between the first and second distal end surfaces 352, 353 and the first and second proximal surfaces 366, 367, respectively. The first and second aligned portions 28A, 28B may be arranged at different angled orientations relative to each other.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A vascular closure system, comprising:
   a body portion having a distal end surface;
   an anchor positionable through a vessel puncture in a vessel wall of a vessel, the anchor defining a vessel contact surface when in an expanded position, wherein withdrawal of the anchor proximally when in the expanded position captures a portion of the vessel wall between the vessel contact surface and the distal end surface to orient the portion of the vessel wall;
a suture carrying portion positionable through the vessel puncture and carrying at least one suture member, the suture carrying portion extending from the body portion distal to the anchor;
a plurality of needles extendable through the portion of the vessel wall adjacent to the vessel puncture, the plurality of needles being configured to connect to the at least one suture member at a position within the suture carrying portion while the at least one suture member is carried within the suture carrying portion;
wherein withdrawal of the plurality of needles through the portion of the vessel wall positions the at least one suture member through the portion of the vessel wall.

2. A vascular closure system according to claim 1 wherein the plurality of needles are arranged non-perpendicular to a longitudinal axis of the vessel.

3. A vascular closure system according to claim 1, wherein the body portion is arranged at an angle relative to the vessel wall prior to capturing a portion of the vessel wall between the vessel contact surface and the distal end surface.

4. A vascular closure system according to claim 1 wherein the plurality of needles connect to the at least one suture member with at least one suture connector mounted to the at least one suture member.

5. A vascular closure system according to claim 1, further comprising a handle positioned at a proximal end of the body portion, and first and second actuators mounted to the handle, the first actuator being operable to expand and retract the anchor within the vessel, and the second actuator being operable to advance and withdraw the plurality of needles.

6. A vascular closure system according to claim 1 wherein the plurality of needles includes two pairs of needles, and the at least one suture member includes a pair of suture members, wherein a separate one of the two pairs of needles being connecting to one of the suture members.

7. A vascular closure system according to claim 1 wherein the body portion is continuous with the suture carrying portion, and the anchor expands radially outward from the suture carrying portion.

8. A vascular closure system according to claim 1 wherein at least one of the plurality of needles extends perpendicularly through the portion of the vessel wall at any angled arrangement of the body portion relative to a longitudinal axis of the vessel.

9. A vascular closure system according to claim 1, wherein the anchor includes first and second anchor arms operable between recessed and radially expanded positions.

10. A vascular closure system according to claim 9, wherein the first anchor arm defines a first vessel contact surface, and the second anchor arm defines a second vessel contact surface, wherein the first and second vessel contact surfaces are arranged at different axial positions relative to the distal end surface of the body portion.

11. A vascular closure system according to claim 10, wherein the body portion includes a first distal end surface aligned with the first vessel contact surface, and a second distal end surface aligned with the second vessel contact surface, wherein the first and second distal end surfaces are arranged at axially spaced apart positions.

12. A vascular closure system according to claim 9, wherein the first anchor arm defines a first vessel contact surface arranged perpendicular to a longitudinal axis of the body portion, and the second anchor arm defines a second vessel contact surface arranged at a non-perpendicular angle relative to the longitudinal axis of the body portion.

13. A vascular closure system according to claim 9, wherein the body portion includes a taper surface at a distal end of the body portion, the taper surface extending proximally from the distal end surface.

14. A vascular closure system according to claim 1, wherein the body portion includes first and second distal end surfaces, the first distal end surface being arranged perpendicular to a longitudinal axis of the body portion, and the second distal end surface being arranged at a non-perpendicular angle relative to the longitudinal axis of the body portion.

15. A vascular closure device, comprising:
a body portion positioned outside a vessel and arranged at an angle relative to a longitudinal axis of the vessel;
a suture carrying portion extending distally from the body portion;
an expandable anchor positionable through a puncture in the vessel and operable to capture a portion of the vessel between the body portion and the anchor and arrange the portion of the vessel at an angle relative to a length dimension of the body portion;
first and second suture members extending from the body portion within the suture carrying portion, the first and second suture members configured to be positionable within the vessel distal to the expandable anchor;
first and second pairs of needles operable to advance through the portion of the vessel adjacent to the puncture, connect to the first and second suture members at a position within the suture carrying portion, and be withdrawn through the portion of the vessel to position the first and second suture members through the portion of the vessel.

16. A vascular closure device according to claim 15 further comprising a suture carrying portion configured to retain the first and second suture members at a location distal of the anchor.

17. A vascular closure device according to claim 15 wherein the anchor is movable between a retracted position within the body portion and an expanded position distal of the body portion.

18. A vascular closure device according to claim 17 wherein the anchor in the expanded position is operable to arrange the portion of the vessel at a perpendicular angle relative to the length dimension of the body portion.

19. A vascular closure device according to claim 15 wherein the body portion includes a handle and first and second actuators, the first actuator being operable to move the anchor between retracted and expanded positions within the vessel, and the second actuator being operable to move the plurality of needles between withdrawn and advanced positions.

20. A method of closing a vascular opening in a vessel wall, comprising:
providing a vascular closure device having a body portion, an expandable anchor, a suture carrying portion extending from the body portion, and a plurality of needles, the suture carrying portion including at least one length of suture;
inserting the anchor and suture carrying portion through the vascular opening;
operating the anchor into an expanded position;
capturing a portion of the vessel wall between the anchor and a distal end of the body portion and orienting the portion of the vessel wall relative to the distal end of the body portion;

advancing the plurality of needles through the portion of the vessel wall adjacent to the vascular opening;

connecting the plurality of needles to the at least one length of suture at a position within the suture carrying portion distal to the anchor;

withdrawing the plurality of needles to pull the at least one length of suture through the vessel wall adjacent to the vascular opening;

operating the anchor into a retracted position;

removing the anchor and suture carrying portion from the vascular opening.

21. The method of claim 20, further comprising arranging the body portion at a non-perpendicular angle relative to the vessel wall before capturing the vessel wall.

22. The method of claim 20, wherein capturing the vessel wall includes arranging a portion of the vessel wall that is captured at a perpendicular angle relative to a longitudinal axis of the body portion for any angled position of the body portion relative to a remaining portion of the vessel wall.

23. The method of claim 20, wherein the body portion includes a handle and first and second actuators mounted to the handle, the method including operating the first actuator to operate the anchor into expanded and retracted positions, and operating the second actuator to advance and withdraw the plurality of needles.

24. The method of claim 20, wherein the plurality of needles includes first and second pairs of needles, and at least one length of suture includes first and second lengths of suture, wherein connecting the plurality of needles to the at least one length of suture includes connecting the first pair of needles to opposing ends of the first length of suture, and connecting the second pair of needles to opposing ends of the second length of suture.

25. The method of claim 20, wherein withdrawing the plurality of needles to pull the at least one length of suture through the vessel wall includes pulling suture through four separate holes in the vessel wall formed by the plurality of needles.

26. The method of claim 20, wherein the expandable anchor defines first and second vessel contact surfaces arranged facing the portion of the vessel wall and offset axially from each other, and capturing a portion of the vessel wall between the anchor and a distal end of the body portion includes positioning portions of the vessel wall at different axial positions relative to the body portion.

27. The method of claim 20, wherein the expandable anchor defines first and second vessel contact surfaces arranged facing the portion of the vessel wall, the first and second vessel contact surfaces being arranged at different angled orientations relative to each other, and capturing a portion of the vessel wall between the anchor and a distal end of the body portion includes positioning portions of the vessel wall at different angled orientations relative to the body portion.

28. The method of claim 20, wherein the distal end of the body portion defines first and second distal end surfaces arranged facing the portion of the vessel wall and offset axially from each other, and capturing a portion of the vessel wall between the anchor and a distal end of the body portion includes positioning portions of the vessel wall at different axial positions relative to the body portion.

29. The method of claim 20, wherein the distal end of the body portion defines first and second distal end surfaces arranged facing the portion of the vessel wall, the first and second distal end surfaces being arranged at different angled orientations relative to each other, and capturing a portion of the vessel wall between the anchor and a distal end of the body portion includes positioning portions of the vessel wall at different angled orientations relative to the body portion.

30. A method of operating a vascular closure device, comprising:

providing the vascular closure device with a body portion, an expandable anchor, a suture carrying portion, and a plurality of needles, the suture carrying portion including at least one suture and being positioned distal of the anchor;

moving the anchor into an expanded position;

withdrawing the anchor proximally toward the body portion when in the expanded position;

advancing the plurality of needles from the body portion into contact with the suture carrying portion distal to the anchor to connect with the at least one suture at a position within the suture carrying portion;

withdrawing the plurality of needles to move the at least one suture proximally into the body portion;

moving the anchor distally while in an at least partially expanded position;

moving the anchor into a retracted position.

31. The method of claim 30, wherein the anchor includes first and second anchor portions that define first and second vessel contact surfaces, and moving the anchor into an expanded position includes arranging the first and second vessel contact surfaces at axially spaced apart positions relative to the body portion.

32. The method of claim 30, wherein the body portion defines first and second body surfaces arranged facing the anchor when the anchor is in the expanded position, the first and second body surfaces offset axially from each other, and moving the anchor into an expanded position includes arranging a first portion of the anchor in alignment with the first body surface and arranging a second portion of the anchor in alignment with the second body surface.

33. The method of claim 30, wherein at least a portion of the anchor facing the body portion is arranged at a non-perpendicular angle relative to a longitudinal axis of the body portion when the anchor is in an expanded position.

* * * * *